(12) United States Patent
Dierkes et al.

(10) Patent No.: US 9,556,525 B2
(45) Date of Patent: Jan. 31, 2017

(54) CERAMIC OR GLASS-CERAMIC ARTICLE AND METHODS FOR PRODUCING SUCH ARTICLE

(75) Inventors: Stephan Dierkes, Bremen (DE); Anne Jans Faber, Veldhoven (NL); Jan Wilkes, Duesseldorf (DE); Mark P. M. Welters, Venlo (NL); Wilhelm Meiners, Aachen (DE); Konrad Wissenbach, Herzogenrath-Kohlscheid (DE)

(73) Assignees: BEGO BREMER GOLDSCHLAEGEREI WILH, HERBST GMBH & CO. KG, Bremen (DE); NEDERLANDSE ORGANISATIE VOOR TOEGEPAST NATUURWETENSCHAPPELIJK ONDERZOEK TNO INNALOX BV, Delft (NL); FRAUNHOFER-GESELLSCHAFT ZUR FOERDERUNG DER ANGEWANDTEN FORSCHUNGE E.V., Munich (DE)

( * ) Notice: Subject to any disclaimer, the term of this patent is extended or adjusted under 35 U.S.C. 154(b) by 1234 days.

(21) Appl. No.: 13/389,789

(22) PCT Filed: Aug. 10, 2010

(86) PCT No.: PCT/EP2010/061637
§ 371 (c)(1),
(2), (4) Date: Apr. 23, 2012

(87) PCT Pub. No.: WO2011/018463
PCT Pub. Date: Feb. 17, 2011

(65) Prior Publication Data
US 2012/0237745 A1    Sep. 20, 2012

(30) Foreign Application Priority Data

Aug. 10, 2009 (EP) .................................. 09167581

(51) Int. Cl.
*B05D 3/06* (2006.01)
*C23C 24/10* (2006.01)
(Continued)

(52) U.S. Cl.
CPC ............... *C23C 24/10* (2013.01); *A61K 6/024* (2013.01); *A61K 6/025* (2013.01); *A61K 6/0215* (2013.01);
(Continued)

(58) Field of Classification Search
CPC ......... C23C 24/00; C23C 24/10; B23K 26/00; B23K 26/08; B23K 26/206; B23K 26/324; B23K 26/3266; B23K 26/3273; B23K 26/345; C04B 35/03; C04B 35/10–35/119; C04B 35/46–35/478; C04B 35/48–35/493; C04B 35/5611; C04B 35/5615; C04B 35/5618; C04B 35/565; C04B 35/581; C04B 35/62222; C04B 35/653; C04B 2235/3217–2235/3224; C04B 2235/3225; C04B 2235/3227; C04B 2235/3231; C04B 2235/3232; C04B 2235/3241–2235/3249; C04B 2235/3281–2235/3282; C04B 2235/3418; C04B 2235/3826–2235/3834; C04B 2235/3843; C04B 2235/3878; B28B 1/00; B28B 1/001; B28B 1/30; B22F 3/105; B22F 3/1055; B22F 3/1058; A61K 6/0205; A61K 6/021; A61K 6/0225; A61K 6/0235; A61K 6/024; A61K 6/025; A61K 6/0255; A61K 6/0273
(Continued)

(56) References Cited

U.S. PATENT DOCUMENTS

| 4,595,663 A | 6/1986 | Krohn et al. |
| 4,814,575 A | 3/1989 | Petitbon |

(Continued)

FOREIGN PATENT DOCUMENTS

| | | |
|---|---|---|
| DE | 2004041633 A1 | 3/2006 |
| EP | 1561839 A1 | 8/2005 |

(Continued)

OTHER PUBLICATIONS

I. Shishkovsky et al.; "Alumina-zirconium ceramics synthesis by selective laser sintering/melting"; Applied Surface Science vol. 254, pp. 966-970 (2007; available online Sep. 6, 2007).*

(Continued)

*Primary Examiner* — Marianne L Padgett
(74) *Attorney, Agent, or Firm* — Duane Morris LLP; J. Rodman Steele, Jr.; Gregory M. Lefkowitz

(57) ABSTRACT

The present invention relates to a method of producing a (shaped) ceramic or glass-ceramic article, involving the steps of: (a) providing a powder or a powder mixture comprising ceramic or glass-ceramic material, (b) depositing a layer of said powder or powder mixture on a surface, (d) heating at least one region of said layer by means of an energy beam or a plurality of energy beams to a maximum temperature such that at least a part of said ceramic or glass-ceramic material in said at least one region is melted and (e) cooling said at least one region of said layer so that at least part of the material melted in step (d) is solidified, such that the layer is joined with said surface in said at least one region. The invention also relates to ceramic or glass-ceramic articles and their use.

16 Claims, 2 Drawing Sheets

(51) Int. Cl.

| | |
|---|---|
| *A61K 6/02* | (2006.01) |
| *A61K 6/027* | (2006.01) |
| *B22F 3/105* | (2006.01) |
| *B23K 26/00* | (2014.01) |
| *B23K 26/08* | (2014.01) |
| *B28B 1/00* | (2006.01) |
| *B29C 67/00* | (2006.01) |
| *C04B 35/109* | (2006.01) |
| *C04B 35/119* | (2006.01) |
| *C04B 35/488* | (2006.01) |
| *C04B 35/653* | (2006.01) |
| *C23C 24/00* | (2006.01) |

(52) U.S. Cl.
CPC ............ *A61K 6/0255* (2013.01); *A61K 6/0273* (2013.01); *B22F 3/105* (2013.01); *B23K 26/00* (2013.01); *B23K 26/08* (2013.01); *B28B 1/00* (2013.01); *B28B 1/001* (2013.01); *B29C 67/0066* (2013.01); *C04B 35/109* (2013.01); *C04B 35/119* (2013.01); *C04B 35/4885* (2013.01); *C04B 35/653* (2013.01); *C23C 24/00* (2013.01); *B22F 3/1055* (2013.01); *C04B 2235/3217* (2013.01); *C04B 2235/3225* (2013.01); *C04B 2235/3244* (2013.01); *C04B 2235/5436* (2013.01); *Y02P 10/295* (2015.11); *Y10T 428/24967* (2015.01); *Y10T 428/2982* (2015.01)

(58) Field of Classification Search
USPC .......... 427/526, 529, 530, 551–559; 264/497, 264/430–434
See application file for complete search history.

(56) References Cited

U.S. PATENT DOCUMENTS

| | | | |
|---|---|---|---|
| 4,863,538 A | 9/1989 | Deckard | |
| 5,393,482 A | 2/1995 | Benda et al. | |
| 5,427,825 A * | 6/1995 | Murnick | B28B 11/044 427/555 |
| 6,215,093 B1* | 4/2001 | Meiners | B22F 3/1055 219/121.61 |
| 6,217,816 B1* | 4/2001 | Tang | B28B 1/00 264/497 |
| 6,767,499 B1 | 7/2004 | Hory et al. | |
| 2006/0119017 A1 | 6/2006 | Tang | |
| 2015/0367415 A1* | 12/2015 | Buller | B23K 26/346 419/53 |
| 2016/0083303 A1* | 3/2016 | Mironets | C04B 35/117 264/497 |
| 2016/0083304 A1* | 3/2016 | Mironets | C04B 35/10 264/497 |
| 2016/0175929 A1* | 6/2016 | Colin | C04B 35/62839 419/23 |

FOREIGN PATENT DOCUMENTS

| | | |
|---|---|---|
| JP | 10-259070 | 9/1998 |
| JP | 2003001368 A | 1/2003 |
| JP | 2003217438 | 7/2003 |
| JP | 2003531034 | 10/2003 |
| JP | 2003534926 | 11/2003 |
| JP | 2007534838 | 11/2007 |
| JP | 2009078558 | 4/2009 |
| WO | 2005095304 A1 | 10/2005 |
| WO | WO 2009/132782 A1 * | 11/2009 ............ C04B 35/109 |

OTHER PUBLICATIONS

A. Larrea et al.; "ZrO2—Al2O3 eutectic plates produced by laser zone melting"; Journal of the European Ceramic Society; vol. 22, issue 2, Feb. 2002; pp. 191-198.*
Rosa I Merino et al.; Ionic conductivity in directionally solidified Al2O3—ZrO2(3% mol Y3O2) near eutectic composites; Solid State Ionics, vol. 178, pp. 239-247 (2007; no month given).*
Backofen et al.; "Superplasticity in Al—Zn Alloy"; Transactions of American Society for Metals; vol. 57; 1964 (no month); pp. 980-989.*
Romero et al.; "Development of Mica Glass—Ceramic Glazes"; Journal of American Ceramic Society; vol. 87, #5, 2004 (no month); pp. 819-823.*
Yekta et al.; "Synthesis of glass-ceramic glazes in the ZnO—Al2O3—SiO2—ZrO2 system"; Journal of the European Ceramic Society; vol. 27; available online Sep. 26, 2006; pp. 2311-2315.*
Patent Cooperation Treaty, International Search Report and Written Opinion from the European Patent Office, in Application PCT/EP2010/061637, by Authorized Officer Arne Nielsen-Hannerup, pp. 1-14 Nov. 2, 2010.

* cited by examiner

CERAMIC OR GLASS-CERAMIC ARTICLE AND METHODS FOR PRODUCING SUCH ARTICLE

CROSS-REFERENCE TO RELATED APPLICATIONS

This application is a §371 national stage entry of International Application No. PCT/EP2010/061637, filed Aug. 10, 2010, which claims priority to European Patent Application No. EP 09167581.9, filed Aug. 10, 2009, the entire contents of which are incorporated herein by reference.

FIELD OF THE INVENTION

The present invention relates to a method of producing a (shaped) ceramic or glass-ceramic article, in particular a dental article or an article for use in the electronic industry, refractory industry, chemicals industry, aerospace industry or food industry. The method involves the steps of: (a) providing a powder or a powder mixture comprising ceramic or glass-ceramic material, (b) depositing a layer of said powder or powder mixture on a surface, (d) heating at least one region of said layer by means of an energy beam or a plurality of energy beams to a maximum temperature such that at least a part of said ceramic or glass-ceramic material in said at least one region is melted and (e) cooling said at least one region of said layer so that at least part of the material melted in step (d) is solidified, such that the layer is joined with said surface in said at least one region. The present invention also relates to the products obtainable by the method of the invention, in particular to ceramic or glass-ceramic articles obtainable by the method. The invention also relates to the use of the product (article) in particular as a dental article or in the electronic industry, refractory industry, chemicals industry, aerospace industry or food industry. The present invention relates to the technical field sometimes referred to as "Melting Layer Manufacturing processes", see G. N. Levy, R. Schindel, J.-P. Kruth, CIRP Ann. Manuf. Technol. 52 (2) 589.

BACKGROUND OF THE INVENTION

Methods of producing ceramic or glass-ceramic articles are well known. The economies associated with conventional part production generally favor the production of large quantities of identical parts. Corresponding methods most of the time require complex processes involving the production of molds or the like. For commercial reasons, these production methods are generally unacceptable for small quantities. For prototyping, the production of small series of ceramic or glass-ceramic articles or the production of a plurality of articles each having different shape, only few economically viable methods are know. Mostly such methods involve a subtractive machining method. In such subtractive machining methods material is cut away from a starting block of material to produce a more complex part. Examples of such methods include: milling, drilling, grinding, lathe cutting, flame cutting, use of an electrical discharge machine etc. The problems associated with these production methods are large initial investment, waste of material and tool wear. The latter is costly and reduces accuracy of the articles produced. One method to produce shaped ceramic or glass-ceramic articles is computer controlled milling of shaped bodies out of the solid ceramic or glass-ceramic material, which inevitably leads to considerable waste that has to be reprocessed at great effort and expense. Also, complicated shapes with deep hollows are not accessible by the aforementioned methods or require complex procedures.

In order to solve these problem free form fabrication methods (solid free form fabrication methods) have been developed. This term relates to a collection of methods that have been successfully applied to produce articles from materials such as metals, plastics, ceramics, and the like. Typical examples are (i) electron beam melting, which involves melting of metal powder and produces substantially void free articles without pores, (ii) laser engineered net shaping, wherein a laser is used to melt metal powder and to deposit it on a substrate and (iii) selective laser sintering (SLS) or selective laser melting (SLM), which uses a laser to fuse powdered nylon, elastomer, metal or ceramic material. SLM usually requires additional processing to produce fully dense parts. For a typical example of a freeform fabrication method see also Griffith et al. "Free form fabrication of metallic components using laser engineered net shapings", Solid free form fabrication symposium, Austin, Tex., Aug. 12-14, 1996.

The automatic construction of physical objects using free form fabrication is called rapid prototyping. Rapid prototyping takes virtual designs from computer aided design (CAD) or animation modeling software or other data that describe the shape of physical objects, transforms them into data of thin, virtual, horizontal cross-sections of said physical objects and builds a new physical object on the basis of the data of the cross-sections.

An apparatus lays down successive layers of liquid, powder, or sheet material, and in this way builds up the new object from a series of said cross-sections. Selective laser melting (SLM) is a special type of rapid prototyping, wherein layers of material (in particular layers of powdered material) are molten and joined by subsequent crystallization. Aspects of rapid prototyping have for example been described in D. T. Pham, S. S. Dimov, Rapid manufacturing, Springer-Verlag, 2001, ISBN 1-85233-360-X.

U.S. Pat. No. 4,863,538 discloses a method of producing an article from plastic, metal or ceramic material by a free form sintering method, i.e. by sequentially sintering a plurality of powder layers to build the desired part in a layer-by-layer fashion. Heating is effected by means of a laser. EP 0 946 325 B1 discloses "Selective Laser Melting" (SLM). Various other publications have been published concerning this type of technology. However, ceramic or glass-ceramic articles produced by such known methods often have a fairly large amount of cracks, fissures and other imperfections, and therefore have inferior properties, especially inferior mechanical properties, inferior biocompatibility, high porosity and the like and are therefore not suited for sophisticated applications, e.g. as dental article or in certain applications in the electronic industry.

The often inferior properties of ceramic or glass-ceramic articles produced by such methods are primarily a result of the very high melting points of ceramic materials. These melting points make rapid rates of heating and cooling of the material necessary and result in large temperature differences among different parts of the articles produced during the production process. This leads to high stresses inside the ceramic or glass-ceramic articles which in turn lead to cracks, fissures and other defects.

Various means to improve the properties of ceramic or glass-ceramic articles have been proposed. U.S. Pat. No. 5,508,489 proposes the use of at least two laser beams to heat the powder, wherein one laser is used to sinter the powder and a defocused laser is used to provide a predetermined temperature gradient between the sintering location and the surrounding powder. This method reduces curling of the produced layers.

U.S. Pat. No. 7,452,500 describes a method, wherein a high-energy beam irradiates predetermined positions of a powder layer a plurality of times, wherein each position is first at least once heated to a temperature below the melting point of the powder material and during the second or a later irradiation heated to a temperature above the melting temperature. In SLM a layer of material is usually heated by means of laser irradiation on only one side of the layer, the side of the layer facing away from the beam is heated solely by heat transfer within the layer, which may be slow compared to the heating rate. A high temperature gradient between the two sides of the layer is the result. This may lead to evaporation, in particular explosive evaporation, on the side of the layer heated by the beam, while the side of the layer facing away from the beam may not even be molten.

U.S. Pat. No. 7,452,500 solves this problem by heating during a plurality of intervals. During the waiting period between two intervals the temperature gradient between the two sides of the layer is reduced by heat transfer, while the beam heats other regions of the layer. Thus the method avoids large temperature differences between the two sides of the layer to be melted, which avoids the risk of evaporation or even explosive evaporation of layer material due to overheating and reduces the time required to make an article. It also leads to reduced stress. An apparatus for free form fabrication is also disclosed in U.S. Pat. No. 7,452,500.

Reference is further made to the following documents:
U.S. Pat. No. 4,814,575 AUS 2006/119017 A1
EP 1 561 839 A1
U.S. Pat. No. 5,393,482 A
U.S. Pat. No. 6,767,499 B1
JP 2003 001368 A
DE 10 2004 041 633 A1
U.S. Pat. No. 4,863,538 A1
WO 2005/095304 A1
WO 0 240 744
EP 0 129 188
EP1 772 210
WO 2004/089 851
DE 10 2005 048 314
SHISHKOVSKY ET AL: "Alumina-zirconium ceramics synthesis by selective laser sintering/melting" APPLIED SURFACE SCIENCE, ELSEVIER, AMSTERDAM, NL, Vol. 254, No. 4, 23. Nov. 2007, Pages 966-970,
MERINO ET AL: "Ionic conductivity in directionally solidified Al2O3-ZrO2(3% mol Y2O3) near eutectic composites" SOLID STATE IONICS, NORTH HOLLAND PUB. COMPANY. AMSTERDAM, NL, Vol. 178, No. 3-4, 6. Mar. 2007, Pages 239-247
WANG A H ET AL: "Microstructural characteristics of Al2O3-based refractory containing ZrO2 induced by CO2 laser melting" APPLIED SURFACE SCIENCE ELSEVIER NETHERLANDS, Vol. 221, No. 1-4, 15. Jan. 2004, Pages 293-301
BOURBAN ET AL: "Solidification microstructure of laser remelted Al2O3-ZrO2 eutectic" ACTA MATERIALIA, ELSEVIER, OXFORD, GB, Vol. 45, No. 12, 1. Dec. 1997, Pages 5069-5075
LARREA A ET AL: "ZrO2-Al2O3 eutectic plates produced by laser zone melting" JOURNAL OF THE EUROPEAN CERAMIC SOCIETY, ELSEVIER SCIENCE PUBLISHERS, BARKING, ESSEX, GB, Vol. 22, No. 2, 1. Feb. 2002, Pages 191-198,
LLorca et al: Progress in Materials Science 51 (2006) Pages 711-809.

However, until to date no method of free form fabrication is known for the preparation of ceramic or glass-ceramic articles with similar or even better material properties than those produced by the above mentioned subtractive machining methods.

SUMMARY OF THE INVENTION

It was an object of the present invention to provide an improved method for the free form production of ceramic or glass-ceramic articles. It was in particular an object of the present invention to provide an improved method for the free form fabrication of ceramic or glass-ceramic articles, which avoids waste of material and which is economically viable for prototype production, for the production of small series or the production of various articles wherein each article has a different shape, and which provides ceramic and glass ceramic articles with improved bending strength, hardness, smoothness of the surface, fracture toughness, fracture strength, biocompatibility and/or reduction of the overall pore volume of the articles. Further, it was in particular an object of the present invention to provide an improved method for the free form fabrication of ceramic or glass-ceramic articles, which allows the production of dense ceramic or glass ceramic material without the necessity of subsequent sintering or a subsequent glass infiltration process. It was also in particular an object of the present invention to provide an improved method for the free form fabrication of ceramic or glass-ceramic articles, which allows the production of ceramic or glass ceramic material with less or even without cracks and fissures and other damages. It was especially an object of the present invention to provide an improved method for the free form fabrication of ceramic or glass-ceramic articles, which allows the production of ceramic or glass-ceramic articles with complex three dimensional structures that cannot be produced by subtractive methods of production. It was a further object of the present invention to provide ceramic or glass-ceramic articles with improved properties produced or producible by a free form production method.

According to a first aspect of the present invention the stated object is achieved by a method of producing a ceramic or glass-ceramic article (preferably a multi-layer article) comprising the steps of:

(a) providing a powder or a powder mixture comprising ceramic or glass-ceramic material, (b) depositing a layer of said powder or powder mixture on a surface, (d) heating at least one region of said layer by means of an energy beam or a plurality of energy beams to a maximum temperature such that at least a part of said ceramic or glass-ceramic material in said at least one region is melted, (e) cooling said at least one region of said layer so that at least part of the material melted in step (d) is solidified, such that the layer is joined with said surface in said at least one region.

Preferably, during solidification in step (e) from the molten ceramic or glass-ceramic material two or more phases of distinct materials crystallize. Typically, in contrast to methods wherein only a single phase crystallizes, articles comprising two or more phases of distinct materials have improved physical, in particular mechanical, properties. Preferred is a method according to the invention (preferably a method characterized in this text as preferred,) wherein the powder or powder mixture consists of ceramic or glass-ceramic material.

The method according to the present invention allows the production of a ceramic or glass-ceramic article from one or more layers of ceramic or glass-ceramic material.

It is especially advantageous that the shape of the ceramic or glass-ceramic article formed in this process can be determined by appropriate selection of the region or regions heated in step (d). In contrast to the subtractive methods no mechanical operations are necessary to determine the shape of the ceramic or glass-ceramic article. In a preferred method according to the present invention (preferably a method characterized in this text as preferred,) the shape of the layer is determined by the region or regions heated in step (d).

The temperature at which at least a part of said powder or powder mixture melts and the temperature at which at least part of the material melted in step (d) is solidified are preferably determined by differential scanning calorimetry.

In a preferred method according to the present invention (preferably a method characterized in this text as preferred,) one, two or a plurality of regions of said layer are not heated in step (d). According to the present invention only the ceramic or glass-ceramic powder of regions heated and melted in step (d) joins with said surface (e.g. a previously deposited and joined layer, see below). In a preferred method according to the present invention (preferably a method characterized in this text as preferred,) the ceramic or glass-ceramic powder of regions not heated in step (d) remains unchanged or at least unchanged to an extent that it can be recycled and used for the purposes of steps (a) to (d) of the present invention without or with little further processing.

Preferred is a method according to the present invention wherein in step (d) during heating said at least one region of said layer by means of an energy beam or a plurality of energy beams to a maximum temperature said ceramic or glass-ceramic material in said at least one region is completely melted. In particular in such a preferred method the complete material melted re-solidifies so that the properties of the article prepared are co-determined by the size and shape of the crystals formed from the melt, wherein the solidification and crystallization process can be precisely controlled by controlling the cooling rate, and customized articles can be prepared.

Preferred is further a method according to the present invention, wherein step (e) comprises cooling said at least one region of said layer below the solidus temperature of the layer material present in said region after step (d), such that the layer is joined with said surface in said at least one region.

In the present text any ceramic or glass-ceramic article produced by a method of the present invention which is used in a further processing step (e.g. a thermal aftertreatment or the repetition of steps (a) to (e) in order to add one or more further layers) is also called "intermediate product".

A preferred method according to the present invention, (preferably a method characterized in this text as preferred,) comprises the successive repetition of steps (a), (b), (d), and (e), wherein the surface of the layer produced by a preceding series of steps (a) to (e) is used in a respective subsequent step (b) as surface for the following layer. This method allows the construction of (multi-layered) articles with complicated shapes by joining as many layers as necessary. It avoids waste of material and is economically viable for prototype production, for the production of small series or the production of various articles wherein each article has a different shape. The method also allows the production of ceramic or glass-ceramic articles with complex three dimensional structures that cannot be produced by subtractive methods of production.

The building time of the ceramic or glass-ceramic articles according to the present invention is an important factor for the determination of the commercial viability of the present process. Two (interdependent) parameters that influence the building time are the cycle time and the height building speed. In a preferred method of the present invention a single cycle of steps (a), (b), (d), and (e) requires less than 5 minutes from the beginning of step (a) to the end of step (e), more preferably less than 2 minutes. Such a short cycle time is favored in order to make the process economically more viable. Parameters that influence the cycle time are for example the size of the area of the surface of the layer deposited in step (b) that is to be melted, the power of the energy beam and the size and the shape of the impact area of the energy beam on the layer deposited in step (b). The expert in the art will choose and, if necessary, optimize these parameters in order to produce the desired ceramic or glass-ceramic articles in a short time.

In a further preferred method of the present invention, the height building speed is 0.5 mm per hour or more, preferably 1.0 mm per hour or more and especially preferred 1.5 mm per hour or more. The height building speed is influenced by the cycle time, the thickness of the layer deposited in step (b), the time needed to deposit the powder or powder mixture in step (b) and other parameters.

As indicated above, production of ceramic or glass-ceramic articles by a free form production method involves several obstacles most of which are related to the very high melting points of ceramic and glass-ceramic materials. The low heat transmission coefficients of these materials add further problems, but also provide some benefits. In order to join the particles of a layer of ceramic and glass-ceramic material (a) with each other and (b) with the surface on which the layer is deposited, the particles often have to be heated to temperatures above 1500° C. or even above 2000° C. Typically, the surface remains at a much lower temperature. At the time of solidification of the melt, the temperature difference between the surface and the solidified layer is often greater than 1000° C., and may be even greater than 1500° C. At least at the end of the process, the final article and therefore the layer will have to be cooled to ambient temperature. The absolute value of the linear expansion (or shortening) of the solidified layer is typically proportional to the temperature difference, in the present case proportional to the temperature difference between the solidus temperature and ambient temperature. The molten parts of said layer will contract considerably in length, while the dimensions of the surface will not be changed to the same extent. This leads to stresses and for example to curling and possibly to delamination of the layer from the surface.

In case heating, (e.g. in step (d)) is applied to the surface of the layer deposited in step (b) (upper surface), the low heat transmission coefficient of ceramic and glass-ceramic materials also makes it difficult to heat the opposed surface facing away from the surface of said layer deposited in step (b) (opposed surface) as the opposed surface is heated solely by heat conduction. This leads to temperature differences between the two sides of the layer which may cause damages to the structure upon cooling.

A further problem is the time required to heat the opposed surface. It is often desired to surface-fuse the layer deposited in step (b) with the surface on which the powder is deposited in step (b) (underlying surface). In order to fuse said upper layer deposited in step (b) with said underlying surface, said opposed surface that is in contact with the underlying surface and said underlying surface must at least partly be molten in said region. Because of low heat transmission coefficients of the ceramic and glass-ceramic materials melting of the opposed surface may take considerable time and may limit the processing speed of the present process.

One method to increase the processing speed (height building speed) is to increase the power of the energy beam(s), to increase the temperature of the upper surface to temperatures higher than said maximum temperature. This increases the temperature differences between the upper surface and the opposed surface, thereby increasing the heat transmission. However, the temperature of the upper surface does preferably not exceed the boiling point of any of the components of the powder or powder mixture. Otherwise the material would merely vaporize without forming a ceramic or glass-ceramic article. The vapor would also form gas bubbles in a remaining melt pool, which after solidification could lead to a higher porosity and therefore a lower bending strength of the ceramic or glass ceramic articles. Using high-energy beams does therefore usually not increase the processing speed in a satisfactory manner and introduces further problems into the process.

Further preferred is therefore a method according to the present invention, which comprises between step (b) and step (d) the following separate step:

(c) preheating of at least one region of said layer to a preheating temperature such that no part of said ceramic or glass-ceramic material in said at least one region is melted.

Herein, the preheating temperature of step (c) is the temperature of the surface of the layer deposited in step (b) after preheating, i.e. at the time the heating in (separate) step (d) begins. Said preheating temperature is lower than said maximum temperature.

The temperature of the powder or powder mixture at the time when heating according to step (d) starts is usually much lower than said maximum temperature, if step (c) is not performed. In such a situation, by heating a certain region of said layer in step (d) a large temperature difference is created between said region and such regions of said layer that are not heated in step (d). After step (d) has ended, parts of the heated region that are close to the non-heated regions will cool down considerably faster than other parts of that region thereby creating mechanical stress and possibly damages in the region and in the whole structure of the solidified layer. Preheating according to step (c) can be used to alleviate temperature differences in said layer, and it therefore reduces mechanical stress and improves the physical and mechanical properties of the ceramic or glass-ceramic articles produced.

Preheating of said layer deposited in step (b) reduces also the difference between (i) the temperature of the opposed surface at the time step (d) begins and (ii) said maximum temperature, thereby reducing heating time and increasing processing speed. If vaporization caused by overheating of the ceramic or glass-ceramic material is avoided or minimized the porosity of the ceramic or glass-ceramic article produced is reduced.

In the second or any following cycle, preheating also leads to heat transfer to the surface material of the layer solidified in step (e) of the preceding cycle. This heat transfer may reduce the cooling rate of the layer solidified in step (e) of the preceding cycle. Faster cooling may lead to larger amounts of amorphous phases in the produced ceramic or glass-ceramic article. A decreased cooling rate will increase the amount of crystalline parts in the ceramic or glass-ceramic article, thereby increasing bending strength, fracture toughness and other physical properties of the ceramic or glass-ceramic article produced. Preheating may therefore improve the quality of the ceramic or glass-ceramic article produced.

In a particularly preferred embodiment preheating is only performed between step (b) and step (d) only. Preheating is typically conducted using a preheating device. According to step (c) preheating may either end at the time heating according to step (d) starts or before heating according to step (d) starts. In the latter case, said powder or powder mixture may cool down to the preheating temperature (see the above definition) before step (d) starts. In an alternative preferred method of the present invention the preheating device used to preheat said layer in step (c) is also applied during one or more other steps of the aforementioned method.

In certain cases preheating is even applied continuously during most of the process or the whole process of producing said ceramic or glass-ceramic article. Therefore, preferred is a method according to the present invention, (preferably a method characterized in this text as preferred,) wherein step (c) is conducted continuously. If steps (a) to (e) are not repeated, step (c) is beginning before step (d) and is ending after step (d). Alternatively, if steps (a) to (e) are repeated, step (c) is beginning before step (d) is conducted for the first time and is ending after step (d) is conducted for the last time. In an even more preferred method according to the present invention, the method comprises the steps of:

(a) providing a powder or a powder mixture comprising ceramic or glass-ceramic material, (b) depositing a layer of said powder or powder mixture on a surface, (d) heating at least one region of said layer by means of an energy beam or a plurality of energy beams to a maximum temperature such that at least a part of said ceramic or glass-ceramic material in said at least one region is melted, (e) cooling said at least one region of said layer so that at least part of the material melted in step (d) is solidified, such that the layer is joined with said surface in said at least one region, and (f) successive repetition of steps (a), (b), (d), and (e) (in this order), wherein the surface of the layer produced by a preceding series of steps (a) to (e) is used in a respective subsequent step (b) as surface for the following layer and the following step:

(c) preheating of at least one region of said layer to a preheating temperature such that no part of said ceramic or glass-ceramic material in said at least one region is melted, is conducted continuously, beginning before step (d) is conducted for the first time and ending after step (d) is conducted for the last time.

In a preferred method according to the present invention, parts of (i) said ceramic or glass-ceramic material in said at least one region, and (ii) the ceramic or glass-ceramic article already produced are preferably only molten when heated in step (d).

In a further preferred method according to the present invention, (preferably a method characterized in this text as preferred,) after step (e) and in case of successive repetitions of steps (a), (b), (d), and (e), after step (e) is conducted for the last time, the following step is conducted:

(g) cooling of the ceramic or glass-ceramic article to ambient temperatures.

In a preferred method of the present invention preheating in step (c) is applied to the whole surface of the layer deposited in step (b). Especially preferred is a method according to the present invention, as aforementioned, wherein continuous preheating is applied to the whole surface of said layer deposited in step (b) and to the whole surface of the ceramic or glass-ceramic article already produced that is not covered by said layer deposited in step (b). A further preferred method according to the present invention is therefore a method as described herein, wherein the preheating is applied continuously during the whole process of producing said ceramic or glass-ceramic article by infrared irradiation or resistance heating to the whole surface of said layer deposited in step (b) and to the part of the ceramic or glass-ceramic article already produced.

In this method it is possible to reduce temperature differences between different regions of the layer deposited in step (b) and between (i) said ceramic or glass-ceramic material in said at least one region, (ii) parts of the ceramic or glass-ceramic article already produced.

The experiments of the inventors showed that the method of producing a ceramic or glass-ceramic article according to the present invention leads to ceramic and glass ceramic articles with high bending strength, high hardness, high fracture toughness and strength and other desirable properties when the whole ceramic or glass ceramic article produced has a homogenous temperature during production of the ceramic or glass ceramic article, respectively. It is even more advantageous when the whole ceramic or glass ceramic article produced has a homogenous and constant temperature during the whole production process of the ceramic or glass ceramic article. Further preferred is therefore a method of the present invention, wherein the temperature of any two parts of the article already produced differ no more than 300° C., preferably no more than 150° C. and especially preferred no more than 50° C. from each other during a period of time beginning before step (d) is conducted for the first time and ending after step (d) is conducted for the last time and even more preferably throughout the whole production process. Especially preferred is a method of the present invention, wherein the article already produced is kept at a constant temperature during a period of time beginning before step (d) is conducted for the first time and ending after step (d) is conducted for the last time and even more preferably throughout the whole production process.

A very preferred method of producing a ceramic or glass-ceramic article comprises the steps of:

(a) providing a powder or a powder mixture comprising ceramic or glass-ceramic material, (b) depositing a layer of said powder or powder mixture on a surface, (c) preheating of at least one region of said layer to a preheating temperature such that no part of said ceramic or glass-ceramic material in said at least one region is melted, (d) heating at least one region of said layer by means of an energy beam or a plurality of energy beams to a maximum temperature such that at least a part of said ceramic or glass-ceramic material in said at least one region is melted, (e) cooling said at least one region of said layer so that at least part of the material melted in step (d) is solidified, such that the layer is joined with said surface in said at least one region, wherein preheating begins before step (b) and is maintained until the article or an intermediate product thereof has been produced (i.e. no further layers need to be deposited), wherein after step (d) the surface and the material deposited and heated thereon in steps (b) and (d) is lowered (e.g. by lowering a build platform or other support means supporting the surface), wherein steps (a), (b), (d) and (e) and the lowering of the surface are repeated until the article or said intermediate product thereof has been produced.

Preferably, after the final repetition of step (e) (continuous) preheating according to step (c) is stopped and the article is cooled down to ambient temperature (e.g. a temperature in the range of from 10 to 30° C.).

Preferred is a method of the present invention, wherein only the powder or powder mixture, said layer and/or said surface is heated in step (c). In a preferred method of the present invention a reaction chamber is used for producing said ceramic or glass-ceramic article. In a further preferred embodiment (preferably a method characterized in this text as preferred,) the whole or parts of the reaction chamber used for the production of the ceramic or glass-ceramic article are preheated continuously by infrared irradiation or resistance heating. In such a method, the whole chamber and its content or parts thereof is kept continuously at a high temperature so that large differences in temperature during the production process can be avoided. In such a preferred method, preferred is that the preheating temperature is less than 1200° C., preferably less than 1050° C. However, preheating of the whole chamber or parts thereof involves a complex and costly apparatus, as all machinery used and all parts of the chamber that are preheated have to be able to withstand high temperatures for an extended period of time.

In a particularly preferred method according to the present invention (more preferably according to any method according to the present invention characterized herein as preferred,) if step (c) is conducted, the energy for preheating in step (c) is directed to the surface of said layer. This allows to define exactly the location the energy is applied to and to apply it close to the location where heating is required. Unnecessary or undesired heating of parts of the apparatus or undesired melting of the parts of the ceramic or glass-ceramic article already produced can be largely avoided.

If step (c) is conducted, further preferred is a method according to the present invention (more preferably according to any method according to the present invention characterized herein as preferred,) wherein in step (c) the layer is preheated by means of an energy beam or a plurality of energy beams. Energy beams can provide a large amount of energy in a short time and are well suited to apply energy to the surface of a solid, as they do not or not to a relevant extent interfere with gas, but can be absorbed by the surface of solids. They are also able to provide a well defined amount of energy to a well defined location with a high energy density, i.e. a well defined, high amount of energy per surface area.

Preferably, in step (c) said energy beam or at least one of said plurality of energy beams is directed to said layer in a predetermined exposure pattern. For example, the exposure pattern defines the shape of the corresponding cross-section of the final ceramic or glass ceramic article. Favorably, in particular when irradiation is performed in a predetermined exposure pattern, said energy beam or at least one of said plurality of energy beams is repeatedly directed to said at least one region of said layer in step (c). The limitation of a slow heat transfer due to a low heat transfer coefficient as discussed above can be overcome by irradiating each region to be heated (and melted) according to step (d) repeatedly, e.g. by preheating (irradiating) once or a plurality of times in step (c) and heating in step (d) so that heat transfer from the irradiated (hot) to the opposed (cold) side of the layer can occur within the respective region of the layer of material during a period or those periods, i.e. after a given preheating treatment in step (c), in which the surface of said region is not irradiated. During said period or periods the energy beam or energy beams can be used to heat or preheat other regions of the layer or other layers. After said period wherein said region is not being irradiated, the beam is redirected to the region to continue and/or complete the preheating process or to conduct step (d). In case of alternating irradiation there is no need to wait during irradiation for time-consuming temperature equalization to occur within the irradiated region. Instead, these temperature equalizations in a certain region can occur after an irradiation step (as part of preheating step (c)) has temporarily ended while another irradiation step in another region is started or continued. Thereby the operation time of the preheating means is optimized and preheating is very uniform.

In this way, the duration of the irradiation of a plurality of regions of the layer is significantly reduced. This alternating irradiation also allows the beam source, e.g. a laser or electron beam source, to be higher powered, thus allowing a greater amount of energy to be delivered to the respective position per time. The risk of explosive vaporization of these particles of material is considerably reduced by directing the beam to a different position after a short period.

Especially preferred is a method according to the present invention (more preferably according to any method according to the present invention characterized herein as preferred,) wherein one, two, a plurality or all regions of said layer are preheated in step (c) and are also heated in step (d). This method also reduces mechanical stress through rapid heating and cooling processes and reduces the risk of explosive vaporization as mentioned above. Herein especially preferred is therefore a method according to the present invention, wherein all regions of said layer heated in step (d) are preheated in step (c). Further preferred is a method according to the present invention, wherein an area of said layer is preheated that comprises all regions heated in step (d).

As described above, in a preferred method according to the present invention, the ceramic of glass-ceramic article is prepared by heating and melting of at least one region each of a plurality of parallel layers of a powder or powder mixture and joining of the melt with the respective underlying surface in order to build up a ceramic or glass ceramic article by successive repetition. The combined heating area is therein the area on the surface provided in step (b) consisting of the orthogonal parallel projection of all regions of said layers heated in the first step (d) and in all successive repetitions of step (d) on the surface provided in step (b). Preferred is a method according to the present invention, wherein at least the combined heating area is preheated in step (c). Further preferred is a method according to the present invention, wherein the method comprises the successive repetition of steps (a), (b), (c), (if preheating is not continuous, as discussed above) (d), and (e) and wherein the surface of the layer produced by a preceding series of steps (a) to (e) is used in a respective subsequent step (b) as surface for the following layer and wherein at least the combined heating area is preheated in step (c). This method allows preheating of every region heated in the first step (d) and every repetition of step (d) by a preheating device that is directed to a constant area during the whole production of the ceramic and glass-ceramic article. Adaption of the preheating device to the various regions heated in step (d) in various layers is not necessary, which simplifies preheating.

Further preferred is a method according to the present invention (more preferably according to any method according to the present invention characterized herein as preferred,) wherein said preheating temperature is in the range of from 40% to 99%, preferably in the range of from 60% to 95% of the minimum temperature ("liquidification temperature") in Kelvin (K) at which a crystalline part of said ceramic or glass-ceramic material in said at least one region is melted. The minimum temperature ("liquidification temperature") at which a crystalline part of said ceramic or glass-ceramic material in said at least one region is melted is preferably determined by differential scanning calorimetry. For certain powders or powder mixtures a preferred preheating temperature is in the range of from 900° C. to 2000° C., preferably in the range of from 1200° C. to 1800° C.

In a preferred method according to the present invention (more preferably according to any method according to the present invention characterized herein as preferred,) said at least one region is preheated in step (c) by at least one defocused energy beam. Defocused energy beams in comparison with focused energy beams spread their power over a wider region of the surface layer thereby reducing the risk of evaporation and explosive evaporation of the powder material. Further preferred is a method according to the present invention, (more preferably according to any method according to the present invention characterized herein as preferred,) wherein in step (c) said at least one region is preheated by laser irradiation, electron irradiation or microwave irradiation, preferably laser irradiation. Especially preferred is a method according to the present invention (more preferably according to any method according to the present invention characterized herein as preferred,) wherein in step (c) said at least one region is preheated by one or more laser beams, preferably laser beams of a laser selected from the group consisting of $CO_2$-laser, Nd: YAG-laser, fiber laser and diode laser, wherein it is further preferred that said laser beam is defocused. Defocused laser beams may have a circular or non-circular laser beam. Defocused laser beams according to the present invention preferably have an impact area on the surface of said layer deposited in step (b) (hereinafter called "effective impact area") of more than 0.196 mm$^2$ (equivalent to the area of a circle with a diameter of 500 µm), more preferably of 0.786 mm$^2$ (equivalent to the area of a circle with a diameter of 1000 µm) or more. Defocused laser beams used for the preheating of large parts or more than half of the surface or the whole of the surface of said layer deposited in step (c) preferably have an impact area on the surface of said layer deposited in step (b) (hereinafter called "effective impact area") of more than 1 cm$^2$, more preferably of 5 cm$^2$ or more and even more preferably of 10 cm$^2$ or more. Especially preferred are defocused laser beams that have an impact area that can cover a square area on the surface of said layer deposited in step (b) of 30 mm×40 mm. Said effective impact area is herein defined as the area (circle if a circular laser beam is used) to which 86% of the power of the laser beam is applied. Preferred according to the present invention are defocused laser beams with a Gaussian profile or a beam profile with a high edge steepness and an otherwise homogenous beam profile, corresponding to a (preferred) homogeneous intensity over the irradiated area.

Preferred is a method according to the present invention including a preheating step (c) (more preferably according to any method according to the present invention characterized herein as preferred,) wherein in step (c) one, two, a plurality or all regions are preheated. Especially preferred is a method according to the present invention (more preferably according to any method according to the present invention characterized herein as preferred,) wherein in step (c) said energy beam or said plurality of energy beams is directed to one, two, a plurality or all regions of said layer in a predetermined exposure pattern.

Further preferred is a method according to the present invention wherein the whole surface or at least 50% of the surface of said layer deposited in step (b) is preheated by a preferably defocused homogenous laser beam and wherein the difference in temperature between different preheated regions of the surface of said layer deposited in step (b) is preferably 300° C. or less, preferably 150° C. or less and especially preferred 50° C. or less. The homogeneous laser beam is thereby preferably produced by use of a homogenization device in order to homogenize the intensity distribution of the laser beam. Especially preferred is the use of diffractive optical structures as homogenization device.

Especially preferred is a method according to the present invention, wherein a defocused homogeneous ($CO_2$-)laser beam is used in step (c) to preheat at least the combined heating area and preferably the whole surface and wherein the defocused laser beam is applied continuously during the whole process of producing said ceramic or glass-ceramic article until step (d) and preferably until step (e) is performed for the last time.

In a preferred method according to the present invention (more preferably according to any method according to the present invention characterized herein as preferred,) heating and, if appropriate, preheating is conducted such that the powder or powder mixture in some or all regions that are not heated in step (d) (whether heated in step (c) or not) does not sinter or at least does not sinter to an extent that makes recycling for further use as powder or powder mixture in a method of the present invention impossible. In a preferred method according to the present invention, (more preferably according to any method according to the present invention characterized herein as preferred), heating and, if appropriate preheating is conducted such that that the powder or powder mixture in some or all regions that are not heated in step (d) (whether heated in step (c) or not) is not changed in its relevant chemical or physical properties, especially not changed in chemical composition, particle size and/or flow characteristics. This allows the recycling of the powder or powder mixture and contributes to the commercial viability of the method.

Preferred is a method of the present invention, (more preferably according to any method according to the present invention characterized herein as preferred,) wherein the mode of application of energy during preheating in step (c) to said layer provided in step (b) is not identical to, i.e. differs in at least one aspect from the mode of application of energy during heating in step (d) to said layer provided in step (b), i.e. the application of energy during preheating and heating is preferably not one and the same continuous process. In particular preferred is a method of the present invention, wherein the amount of energy per volume and time or the amount of energy per surface area and time applied to at least one region of said layer provided in step (b) differs for least one period of time during preheating in step (c) from the amount of energy per volume and time or the amount of energy per surface area and time, respectively, applied to the same region of said layer provided in step (b) during heating in step (d).

Especially preferred is a method of the present invention, wherein preheating in step (c) is performed by a defocused energy beam and heating in step (d) is performed by a focused energy beam. Even more preferred is a method of the present invention, wherein preheating in step (c) is performed by a defocused laser beam or a microwave beam and heating in step (d) is performed by a focused laser beam. Most preferred is a method of the present invention, wherein preheating in step (c) is performed by a defocused laser beam and heating in step (d) is performed by a focused laser beam.

Especially preferred is a method according to the present invention, (more preferably according to any method according to the present invention characterized herein as preferred,) wherein said powder or powder mixture comprises components that form an eutectic system with each other. Eutectic systems have a lower melting point than any of their constituents. The presence of a eutectic system in said powder or powder mixture may therefore reduce the temperature necessary to melt said layer, and therefore a reduced maximum temperature may be used in step (d). A reduced temperature leads to reduced temperature differences and therefore to advantageous physical properties of the ceramic or glass ceramic articles, as discussed in other parts of the present text. It leads especially to a reduction in the amount of cracks, fissures and other damages. Eutectic systems also have a higher difference between melting (liquidus) temperature and evaporation temperature, thereby lowering the risk of evaporation, as discussed above.

Particular preferred is a method of producing a ceramic or glass-ceramic article comprising the steps of:

(a) providing a powder or a powder mixture of ceramic or glass-ceramic material, (b) depositing a layer of said powder or powder mixture on a surface, (c) preheating of at least one region of said layer to a preheating temperature such that no part of said powder or powder mixture in said at least one region is melted, (d) heating at least one region of said layer by means of an energy beam or a plurality of energy beams to a maximum temperature such that at least a part of said powder or powder mixture in said at least one region is melted, (e) cooling said at least one region of said layer so that at least part of the material melted in step (d) is solidified, such that the layer is joined with said surface, wherein said powder or powder mixture comprises components that form an eutectic system with each other.

Statements made above regarding preferred embodiments of methods of the present invention apply also to this aspect of the invention.

In the present text an eutectic system is a group of compounds, wherein the equilibrium phase (melt) diagram of a mixture consisting of all compounds of this group has an eutectic point. An eutectic mixture has the mixing ratio of the components of an eutectic system at the eutectic point.

Preferably, when said powder or powder mixture comprises components that form an eutectic system with each other said powder or powder mixture comprises two, three or more ceramic components that form an eutectic system with each other. The use of ceramic components forming an eutectic system leads to an improved chemical resistance and to improved applicability at high temperatures of the produced article, in comparison with non-ceramic materials forming an eutectic system.

More preferably, said powder or powder mixture comprises two, three or more ceramic components that form an eutectic system with each other, such that during solidification in step (e) from the molten ceramic or glass-ceramic material at the eutectic point of said eutectic system two or more phases of distinct materials crystallize. Generally, in contrast to methods wherein only a single phase crystallizes, articles comprising two or more phases of distinct materials have improved physical, in particular mechanical, properties. As the two or more phases of distinct material (at least partially) crystallize at the eutectic point (i.e. simultaneously) the resultant crystals are fine crystals providing an article with further improved physical, in particular mechanical, properties. In preferred methods of the present invention the process conditions and the materials are selected such that a microstructure comprising fine grains (in particular eutectic crystals) with grain sizes smaller than 1 µm is achieved, at least in fractions of the produced article. Depending on the composition of the ceramic or glass-ceramic material in the powder or the powder mixture the fine grains can form a matrix in which larger crystals are embedded (this will many times be the case if a composition is used which is not identical with the composition at the eutectic point). Herein, phases of distinct materials are phases having a different chemical composition (like e.g. $Al_2O_3$ and $ZrO_2$) and are not only distinct due to a difference in the respective modification (as would be the case with cubic and tetragonal $ZrO_2$).

Further preferably, said powder or powder mixture comprises two, three or more ceramic components that form an eutectic system with each other, such that during solidification in step (e) from the molten ceramic or glass-ceramic material at the eutectic point of said eutectic system two or more phases of distinct materials crystallize, wherein the total fraction by weight of said two, three or more ceramic components that form said eutectic system with each other is at least 50%, preferably at least 70%, more preferably at least 80%, of the powder or powder mixture. In many cases the produced article has favorable properties (physical, mechanical) if the amount of eutectic crystals is high.

Even further preferably at least one, preferably all, of the ceramic components forming said eutectic system with another ceramic component are selected from the group consisting of $Al_2O_3$, $ZrO_2$, $Y_2O_3$, $Na_2O$, $Nb_2O_5$, $La_2O_3$, CaO, SrO, $CeO_2$, MgO, $SiO_2$, $TiO_2$, $Cr_2O_3$, CuO, $Eu_2O_3$, $Er_2O_3$, CoO, $Gd_2O_3$, the mixed oxides thereof (especially $MgAl_2O_4$ $Y_3Al_5O_{12}$, $Er_3Al_5O_{12}$, $NiAl_2O_4$, $LaAlO_3$ and $La_2ZrO_7$), SiC, TiC, $Si_3N_4$ and AlN.

Herein especially preferred is a method according to the present invention which comprises one or more repetitions of steps (a) to (e), wherein the surface of the layer produced by each preceding series of steps (a) to (e) is used in a respective subsequent step (b) as surface for the following layer.

In a preferred method according to the present invention (preferably a method characterized in this text as preferred,) the preheating temperature is lower than the liquidus temperature, preferably lower than the solidus temperature of said ceramic or glass-ceramic material. In a further preferred method according to the present invention, (preferably a method characterized in this text as preferred,) the preheating temperature is lower than said maximum temperature.

Preferred is a method according to the present invention, wherein said powder or powder mixture comprises components that form an eutectic system with each other, (more preferably according to any method according to the present invention characterized herein as preferred,) wherein in step (d) heating is conducted such that all components of said eutectic system are present in the melt. It is further preferred, that the maximum temperature is higher than the melting point of the highest melting component of the eutectic system. Thereby all components of the eutectic systems are present in the melt. Especially preferred is a method according to the present invention (more preferably according to any method according to the present invention characterized herein as preferred,) wherein in step (d) heating is conducted such that all components of said eutectic system are present in the melt and wherein in step (e) at least a part of the components of the eutectic system in the melt crystallizes as eutectic mixture. This can for example be achieved by providing a powder or powder mixture with a high proportion of the compounds of the eutectic system and by providing a powder or powder mixture, wherein the compounds of the powder or powder mixture that are part of the eutectic system are present in a weight ratio that is similar to their weight ratio in the eutectic mixture. The crystallization of eutectic mixtures leads to very fine crystals in the crystallized layer and therefore to ceramic or glass-ceramic articles with a high bending strength and a high fracture toughness and other improved physical properties.

Further preferred (generally, not only in the preferred methods already disclosed above) is a method according to the present invention (more preferably according to any method according to the present invention characterized herein as preferred,) wherein at least 50 percent by weight, preferably at least 70 percent by weight, especially preferred at least 80 percent by weight, of said powder or powder mixture consist of components that form an eutectic system with each other.

Especially preferred is a method according to the present invention (more preferably according to any method according to the present invention characterized herein as preferred,) wherein for each component of said eutectic system the fraction by weight of the component, based on the weight of the eutectic system in the powder or powder mixture, is at least 25%, preferably at least 50%, especially preferred at least 70% and most preferred at least 90% of the fraction by weight of the same component in the eutectic mixture of said eutectic system.

The use of a powder or a powder mixture containing components that form an eutectic system with each other has several advantages. A melted mass of an eutectic mixture crystallizes in very fine crystals often of a size of 1 µm or less. The crystals are typically much smaller than crystals that derive from crystallization of non eutectic mixtures. This leads to a dense and homogeneous packing of crystals in the ceramic or glass-ceramic article and an improvement of the bending strength, hardness and smoothness of the surface, fracture toughness, fracture strength, biocompatibility and to a reduction of the overall pore volume. In addition the melting and freezing temperature of eutectic mixtures are lower than those of the single components, so that said maximum temperature can be lowered and formation of cracks, fissures and other damages is reduced.

Preferred is further a method according to the present invention (more preferably according to any method according to the present invention characterized herein as preferred,) wherein said powder or powder mixture comprises one or more compounds selected from the group consisting of $Al_2O_3$, $ZrO_2$, $Y_2O_3$, $Na_2O$, $Nb_2O_5$, $La_2O_3$, CaO, SrO, $CeO_2$, MgO, $SiO_2$, $TiO_2$, $Cr_2O_3$, CuO, $Eu_2O_3$, $Er_2O_3$, CoO, $Gd_2O_3$, the mixed oxides thereof, SiC, TiC, $Si_3N_4$ and AlN. More preferred is a method according to the present invention, preferably as characterized herein before, (more preferably according to any method according to the present invention characterized herein as preferred,) wherein at least 50 percent by weight, preferably at least 70 percent by weight, more preferably at least 80% by weight, of said powder or powder mixture consist of one or more compounds selected from the group consisting of $Al_2O_3$, $ZrO_2$, $Y_2O_3$, $Na_2O$, $Nb_2O_5$, $La_2O_3$, CaO, SrO, $CeO_2$, MgO, $SiO_2$, $TiO_2$, $Cr_2O_3$, CuO, $Eu_2O_3$, $Er_2O_3$, CoO, $Gd_2O_3$, the mixed oxides thereof (especially $MgAl_2O_4$, $Y_3Al_5O_{12}$, $Er_3Al_5O_{12}$, $NiAl_2O_4$, $LaAlO_3$ and $La_2ZrO_7$), SiC, TiC, $Si_3N_4$ and AlN.

Further preferred is a method according to the present invention (more preferably according to any method according to the present invention characterized herein as preferred,) wherein at least 50 percent by weight, preferably at least 70 percent by weight of said powder or powder mixture consist of one or more oxides selected from the group consisting of $ZrO_2$, $Al_2O_3$, $SiO_2$, MgO, $Y_2O_3$, $Cr_2O_3$, $Na_2O$, $TiO_2$, $La_2O_3$, and the mixed oxides thereof, especially $MgAl_2O_4$.

Especially preferred is a method according to the present invention, (more preferably according to any method according to the present invention characterized herein as preferred,) wherein said powder or powder mixture comprises $ZrO_2$ and $Al_2O_3$. Preferably at least 50 percent by weight and more preferably at least 70 percent by weight of said powder or powder mixture consist of $ZrO_2$ and $Al_2O_3$.

Preferred is a method according to the present invention, (more preferably according to any method according to the present invention characterized herein as preferred,) wherein said powder or powder mixture comprises $ZrO_2$ and $Al_2O_3$, and wherein the mixing ratio by weight of $ZrO_2$ to $Al_2O_3$ is in the range of from 1:4 to 4:1, preferably in the range of from 3:7 to 7:3.

Particularly preferred is a method according to the present invention which in addition to steps (a), (b), (d), and (e) comprises a preheating step (c) (for preferred preheating steps see above), and the successive repetition of steps (a), (b), (d), and (e), wherein the surface of the layer produced by a preceding series of steps (a) to (e) is used in a respective subsequent step (b) as surface for the following layer.

In the particularly preferred method said powder or powder mixture comprises components that form an eutectic system with each other (for details of preferred powders or powder mixtures see above), and at least 50 percent by weight, preferably at least 70 percent by weight of said powder or powder mixture consist of one or more compounds selected from the group consisting of $Al_2O_3$, $ZrO_2$, $Y_2O_3$, $Na_2O$, $Nb_2O_5$, $La_2O_3$, CaO, SrO, $CeO_2$, MgO, $SiO_2$, $TiO_2$, $Cr_2O_3$, CuO, the mixed oxides thereof, especially $MgAl_2O_4$, SiC, TiC, $Si_3N_4$ and AlN (for details of preferred powders or powder mixtures see again above).

A preferred method of producing a ceramic or glass-ceramic article thus comprises the steps of:

(a) providing a powder or a powder mixture comprising ceramic or glass-ceramic material, (b) depositing a layer of said powder or powder mixture on a surface, (d) heating at least one region of said layer by means of an energy beam or a plurality of energy beams to a maximum temperature such that at least a part of said ceramic or glass-ceramic material in said at least one region is melted, (e) cooling said at least one region of said layer so that at least part of the material melted in step (d) is solidified, such that the layer is joined with said surface in said at least one region wherein the method includes a preheating step (c) wherein in step (c) one, two, a plurality or all regions are preheated, wherein the method comprises the successive repetition of steps (a), (b), (d), and (e), wherein the surface of the layer produced by a preceding series of steps (a) to (e) is used in a respective subsequent step (b) as surface for the following layer wherein said powder or powder mixture comprises components that form an eutectic system with each other, wherein at least 50 percent by weight, preferably at least 70 percent by weight of said powder or powder mixture consist of one or more compounds selected from the group consisting of $Al_2O_3$, $ZrO_2$, $Y_2O_3$, $Na_2O$, $Nb_2O_5$, $La_2O_3$, CaO, SrO, $CeO_2$, MgO, $SiO_2$, $TiO_2$, $Cr_2O_3$, CuO, the mixed oxides thereof, especially $MgAl_2O_4$, SiC, TiC, $Si_3N_4$ and AlN.

In order to limit the time needed to melt said region of said layer, the use of powerful energy beams is desirable according to the present invention. However, as described above, this entails the risk of evaporation of layer material due to overheating. $ZrO_2$ has a much higher melting point than $Al_2O_3$. In an economic process powerful and fast heating is required for melting $ZrO_2$ in step (d). $Al_2O_3$ may already evaporate in part before the $ZrO_2$ is melted to the extent necessary. If an eutectic mixture of $Al_2O_3$ and $ZrO_2$ is comprised in said powder or powder mixture, part of the $Al_2O_3$ may evaporate during the process in particular in step (d)) such that during step (e) and in the final product the proportion of $Al_2O_3$ relative to $ZrO_2$ may be smaller than in the eutectic mixture. It may therefore be necessary to provide a powder or powder mixture in step (a) that has a higher proportion of $Al_2O_3$ relative to $ZrO_2$ than the eutectic mixture of the two components, in order to consider evaporation. The same applies to other eutectic systems. For the eutectic system consisting of $Al_2O_3$ and $ZrO_2$ it is preferred that $Al_2O_3$ is present in an amount in weight percent that is higher than in the eutectic mixture, preferably up to 7.5% by weight or about 7.5% by weight based on the overall amounts of $Al_2O_3$ and $ZrO_2$ higher than in the eutectic mixture. The eutectic mixture of $Al_2O_3$ and $ZrO_2$ consists of 42.6 percent by weight of $ZrO_2$ and 57.4 percent by weight of $Al_2O_3$. A preferred method according to the present invention (more preferably according to any method according to the present invention characterized herein as preferred,) is a method, wherein said powder or powder mixture comprises $ZrO_2$ and $Al_2O_3$, and wherein the mixing ratio by weight of $ZrO_2$ to $Al_2O_3$ is in the range of from 30:70 to 42.6:57.4, preferably of from 35:65 to 42.6:57.4 and especially preferred in the range of from 39:61 to 42.6:57.4.

Particularly preferred, in particular if evaporation is avoided, is a method according to the present invention, preferably as characterized herein before (more preferably according to any method according to the present invention characterized herein as preferred,) wherein said powder or powder mixture comprises $ZrO_2$ and $Al_2O_3$, and wherein the mixing ratio by weight of $ZrO_2$ to $Al_2O_3$ is 42.6 to 57.4 (eutectic mixture). Further preferred is a method according to the present invention (more preferably according to any method according to the present invention characterized herein as preferred,) wherein said powder or powder mixture consists of 42.6 percent by weight of $ZrO_2$ and 57.4 percent by weight of $Al_2O_3$, i.e. which consists of the eutectic mixture.

The phenomenon of superplastic deformation in ceramics is well known and described in various publications. For a general overview see Hiraga et al. in "High-strain-rate superplasticity in oxide ceramics", Science and Technology of Advanced materials 8 (2007)578-587) and Dirks-Eicken in "Untersuchungen zur Superplastizität von $Al_2O_3$—$ZrO_2$-Keramiken", Fortschrittsberichte VDI, Grund- und Werkstoffe Nr. 343, VDI-Verlag GmbH, Düsseldorf, 1994. Superplasticity allows the plastic deformation of ceramic articles. Ceramic or glass-ceramic solid bodies comprising or consisting of materials with superplastic properties have the ability to deform and change their crystal alignment to a certain extent. Superplastic properties usually increase with temperature. At ambient temperature superplastic properties are usually not existent in ceramics.

Further preferred is therefore a method according to the present invention, wherein said ceramic or glass-ceramic article produced comprises or consists of material that has superplastic properties at elevated temperature. Ceramic or glass-ceramic articles with superplastic properties prepared by a process according to the present invention alleviate tensile stress through superplastic deformation and develop therefore less or repair cracks, fissures and other damages. Superplastic properties can be expressed by a strain-rate-sensitivity-parameter m as disclosed in Dirks-Eicken in "Untersuchungen zur Superplastizität von $Al_2O_3$—$ZrO_2$-Keramiken", Fortschrittsherichte VDI, Grund- und Werkstoffe Nr. 343, VDI-Verlag GmbH, Düsseldorf, 1994, especially page 55 and the documents cited therein. Especially preferred is method according to the present invention (more preferably according to any method according to the present invention characterized herein as preferred,) wherein the material or at least part of the material (solidified in step (e) has an m value maximum in the temperature range of from 1350° C. to 1500° C. of at least 0.5, preferably of at least 0.75.

One requirement for superplasticity is sufficiently small crystal sizes. Eutectic mixtures lead to small crystal sizes, as discussed above. A method according to the present invention, as described above, wherein said powder or powder mixture comprises components that form an eutectic system with each other, may therefore yield ceramic or glass-ceramic articles consisting of material with superplastic properties, thereby reducing cracks, fissures and other damages and improving the physical properties, of the final products.

Mixtures of $Al_2O_3$ and $ZrO_2$ show superplastic properties at high temperatures. The superplastic properties of mixtures of $Al_2O_3$ und $ZrO_2$ are enhanced by addition of MgO, $SiO_2$, Spinell ($MgAl_2O_4$) or Mullite ($SiO_2$—$Al_2O_3$). Especially preferred is a method according to the present invention, (more preferably according to any method according to the present invention characterized herein as preferred,) wherein said powder or powder mixture comprises $ZrO_2$ and $Al_2O_3$ and one or more compounds selected from the group consisting of MgO, $SiO_2$, Spinell ($MgAl_2O_4$) and Mullite ($SiO_2$—$Al_2O_3$). MgO is preferably present in an amount of up to 5%. $SiO_2$ is preferably present in an amount of up to 5%. Spinell ($MgAl_2O_4$) is preferably present in an amount of up to 35%, and Mullite ($SiO_2$—$Al_2O_3$) is preferably present in an amount of up to 25%.

The (efficient) relief of tensile stresses through superplasticity is a process that requires a certain amount of time. If the melt is crystallized and cooled in step (e) at a very fast rate to below the temperature that is required for an efficient relief of tensile strength through superplasticity, cracks, fissures and other damages may occur in the ceramic or glass-ceramic article. Therefore all measures that lead to higher temperatures in the surrounding materials and thereby lead to slower cooling of the layer solidified in step (e) may lead to an extension of the time where the layer solidified in step (e) is in the temperature range that allows superplastic deformation. This in turn may improve the physical properties such as the bending strength of the final ceramic or glass ceramic article.

It has been discussed above that preheating may be performed in step (c). Preheating also leads to heat transfer to the surface material of the layer solidified in step (e) of the preceding cycle. This heat transfer may keep the temperature of the layer deposited in the previous cycle for a longer time in the temperature range that allows for an efficient relief of tensile stress by means of superplastic deformation. This is especially true if the preheating is applied continuously during the whole process of producing said ceramic or glass-ceramic article. Preheating of said powder or powder mixture before step (b) to a powder preheating temperature or preheating of said surface before step (b) and/or heating and/or insulation of the reaction chamber as discussed below may have a similar effect.

Similar arguments can be made for sintering and diffusion.

Therefore, in a preferred method according to the present invention, the following step is performed:
keeping for a period of time the intermediate product at a temperature where at least part of the material it comprises shows superplastic properties, preferably at a temperature of from 1350° C. to 1500° C., wherein the material or at least part of the material solidified in step (e) has a m value of 0.5 or more, preferably 0.75 or more. The period of time will typically be selected such that superplastic deformation (relaxation) can occur.

Typically the method according to the present invention is performed in air. However, if the powder or powder mixture or a part of the ceramic or glass-ceramic article contains components that are sensitive to air under the conditions of the process and that should be retained in the product, an inert gas is used. Examples for air sensitive components are carbides and nitrides. An inert gas may also be used if parts of the apparatus are sensitive to air under the conditions of the process or for other reasons. An example for an air sensitive part of the apparatus is a scraper consisting of or including carbon fiber material. Thus, preferred is further a method according to the present invention wherein at least step (d) is performed in an atmosphere of an inert gas, preferably selected from the group consisting of nitrogen, argon and helium.

As described above, for commercial viability it is important that a single cycle of successive repetition of steps (a), (b), (d), and (e) requires as little time as possible. It is therefore preferred to start with a new cycle before all regions of the layer of the previous cycle are still at an elevated temperature. However, deposition of a powder of powder mixture in step (b) with a high temperature difference to the material of a region of the layer of the previous (preceding) cycle causes a temperature shock to the material of a region of the layer of the previous cycle leading to rapid cooling and in turn to cracks, fissures and other damages.

Preferred is therefore a method according to the present invention (more preferably according to any method according to the present invention characterized herein as preferred,) comprising the following separate step:
Preheating of said powder or powder mixture before step (b) to a powder preheating temperature, such that no part of said ceramic or glass-ceramic material is melted.

Herein, the powder preheating temperature is the temperature of the powder or powder mixture after step (a), i.e. at the time the powder or powder mixture is being deposited on said surface in step (b). In a particularly preferred method according to the present invention, said powder preheating temperature is in the range of from 30% to 90%, preferably of from 40% to 70% of the temperature in Kelvin where at least a part of said ceramic or glass-ceramic material in said at least one region is melted. In a preferred method according to the present invention said powder preheating temperature is in the range of from 800 to 2000° C., preferably in the range of from 900 to 1500. Further preferred is a method according to the present invention, wherein in step (b) said powder preheating temperature is lower than the temperature of any region of said surface in step (b).

In a preferred method according to the present invention (more preferably according to any method according to the present invention characterized herein as preferred,) said powder or powder mixture is preheated before step (b) by means of an energy radiation, preferably by means of microwave radiation or infrared radiation or a radiant heater.

A temperature shock for the material of the surface in step (b) can be reduced or avoided by any means that reduce the temperature difference between powder or powder mixture and the surface. Preferred is therefore also a method according to the present invention, (more preferably according to any method according to the present invention characterized herein as preferred,) comprising the following step:

Preheating of said surface before step (b) to a surface preheating temperature such that no part of the material of said surface is melted and no part of said ceramic or glass-ceramic material in said powder or powder mixture is melted.

The surface preheating temperature is the temperature of the surface on which the powder or powder mixture is deposited in step (b) at the time the powder or powder mixture is deposited. If steps (a) to (e) are repeated, the "surface" of a subsequent step (b) is typically the surface of the layer joined in a preceding cycle (a) to (e).

Especially preferred is a method according to the present invention (more preferably according to any method according to the present invention characterized herein as preferred,) wherein in step (b) the surface and said powder or powder mixture being deposited on the surface have the same temperature. This can for example be achieved by a method according to the present invention, wherein the whole procedure is performed in an apparatus comprising a chamber which comprises the powder or powder mixture to be used in step (b), the originally provided surface, and the ceramic or glass-ceramic article (intermediate product) so far produced (by repetition of steps (a) to (e)), and wherein the whole chamber and its content are preheated to said same temperature.

The cooling rate of the layer after crystallization in step (e) is a relevant parameter in the method according to the present invention. A fast cooling process favors formation of small crystals in the crystallized layer, which improves the properties of the final product. On the other hand relevant superplasticity, sintering and diffusion is only observed above a certain temperature, and the (efficient) relief of tensile strength through superplasticity, sintering and diffusion is a process that requires a certain amount of time. If the melt is crystallized and cooled in step (e) at a very fast rate to below the temperature that is required for the relief of tensile strength through superplasticity, sintering and/or diffusion, cracks, fissures and other damages may occur in the ceramic or glass-ceramic article. Preferred is therefore a method according to the present invention, (more preferably according to any method according to the present invention characterized herein as preferred,) wherein the layers or the ceramic or glass ceramic article already produced are kept in a temperature range that allows relief of tensile strength through superplasticity, sintering and/or diffusion. However, when the layer is kept at a high temperature over a longer period of time, sintering and/or re-crystallization will occur on a disadvantageous scale. The expert in the art will therefore optimize the temperature of the layer already produced such that re-crystallization is diminished while relief of tensile strength through superplasticity is still possible. The choice of temperature or temperature range depends on the materials used. Examples are given below. For further materials the expert will establish suitable temperatures by means of preliminary tests which include measuring and optimizing the superplasticity of the material and the bending strength or other parameters of the products.

Preferred is a method according to the present invention (more preferably according to any method according to the present invention characterized herein as preferred,) wherein said energy beam or at least one energy beam of said plurality of energy beams used in step (d) is a focused energy beam, preferably a focused laser beam of a $CO_2$-laser or a Nd: YAG-laser or a focused electron beam. Most preferred are focused laser beams of $CO_2$-lasers or Nd: YAG-lasers. Focused laser beams according to the present invention preferably have an effective impact area of 0.196 mm$^2$ or less (equivalent to the area of a circle with a diameter of 500 μm), more preferably of 0.0314 mm$^2$ (equivalent to the area of a circle with a diameter of 200 μm) or less. The diameter of a circular focus is therein defined as aforementioned. Preferred according to the present invention are focused laser beams with a Gaussian profile or a top-hat intensity distribution.

Preferred is a method according to the present invention (more preferably according to any method according to the present invention characterized herein as preferred,) wherein the effective impact area of the energy beam used for heating in step (d) is moved over the regions to be heated in step (d) in a plurality of straight parallel lines, wherein each following line is immediately adjacent to the preceding line. Thereby a set of straight parallel tracks of ceramic or glass-ceramic material is produced. It is herein preferred that the offset between two adjacent lines is smaller than the width of the tracks produced such that the tracks overlap to a certain amount to join adjacent tracks with each other in a manner similar to the manner discussed elsewhere in this text for the joining of said layer deposited in step (b) with said surface of the layer produced in the preceding cycle. The necessary amount of overlap depends on the material used, the geometry of the ceramic or glass ceramic article, the cycle time and various other parameters. There may be no overlap necessary or the overlap may be up to half of the width of the tracks produced or even more than that. The expert in the art will determine by preliminary experiments, how much overlap is necessary to achieve the desired properties in the ceramic or glass ceramic article (e.g. bending strength and the like).

If during the melting process parts of the crystal structure of the particles of said powder or powder mixture are retained, i.e. part of the material does not melt, an interface will occur in the re-crystallized layer between the remaining crystal structure of the (not melted) particles of said powder or powder mixture and the material that has crystallized from the melt. Such interfaces are desirable in certain cases and one method according to the present invention (more preferably according to any method according to the present invention characterized herein as preferred,) is a method wherein said region in step (d) is not completely melted so that such interfaces are established.

However, more typical is a method according to the present invention (more preferably according to any method according to the present invention characterized herein as preferred,) wherein in step (d) the powder or powder mixture in said region is completely melted throughout the entire thickness of said layer.

Especially preferred is a method according to the present invention (more preferably according to any method according to the present invention characterized herein as preferred,) wherein in step (d) the powder or powder mixture in said region is (completely) molten and the resulting melt is heated to a temperature that is in the range of from 1.025 to 1.5 times, preferably of from 1.05 to 1.25 times, the temperature in Kelvin of the highest melting component of said powder or powder mixture.

Most preferred is a method according to the present invention (more preferably according to any method according to the present invention characterized herein as preferred,) wherein in step (d) the material of the surface said powder or powder mixture is deposited on in step (b) is partly or completely molten. If the material of said surface is partly or completely molten, the material of said surface and the melt pool(s) derived from melting said regions in step (d) mix with each other. When cooled below their solidus point or melting point, said surface and the molten regions of the layer deposited in step (b) are fused to form one solid ceramic or glass-ceramic body. Preferably the material of the surface said powder or powder mixture is deposited on in step (b) is partly or completely molten by heat transfer from the surface of the layer deposited in step (b).

Not only the chemical composition of the powder or powder mixture as discussed above, but also the properties and condition of the particles constituting the powder or powder mixture have an influence on the properties of the final product. Preferred is a method according to the present invention (more preferably according to any method according to the present invention characterized herein as preferred,) wherein said powder or powder mixture comprises or consists of particles selected from the group consisting of primary particles, agglomerates, or mixtures thereof. Preferred is a method according to the present invention, (more preferably according to any method according to the present invention characterized herein as preferred,) wherein said powder or powder mixture comprises or consists of agglomerates obtained or obtainable by spray drying or powder jetting.

Alternatively preferred is a method according to the present invention (more preferably according to any method according to the present invention characterized herein as preferred,) wherein said powder or powder mixture comprises or consists of primary particles prepared by grinding, solidification from gas phase or dense sintering of agglomerates obtained or obtainable by spray drying or powder jetting. In a powder jetting process, dense sintered agglomerates are prepared by sintering agglomerates consisting of agglomerated units of two or more primary particles in a rotating oven. The process is controlled such that the agglomerated units sinter to form particles (dense sintered agglomerates) that resemble primary particles or are identical to primary particles in structure and/or form, while the agglomerated units do not or not to a large extent sinter with each other to form larger units.

Especially preferred is a method according to the present invention (more preferably according to any method according to the present invention characterized herein as preferred,) wherein said powder or powder mixture consists of particles with a $d_{50}$ particle size in the range of from 1 to 100 µm, preferably in the range of from 15 to 70 µm. The size of the particles has a prominent influence on the minimum thickness of said layer in step (b). If the particle size and therefore the thickness of said layer is too large, and the layer is primarily heated from its surface, melting of the opposed side facing away from the surface will be very slow and melting may be impossible without overheating the surface of said heated region of said layer that is heated which may result in loss of layer material through evaporation. Mixing of viscous melts is difficult and time consuming. Small particles in the stated range allow for a homogeneous melt and do therefore improve the properties of the final product. Throughout this document, if not otherwise mentioned, the particle size of the powder or powder mixture is determined by laser diffraction using a coulter counter.

Preferred is a method according to the present invention (more preferably according to any method according to the present invention characterized herein as preferred,) wherein said powder or powder mixture is a monomodal powder mixture and wherein the respective values for the $d_{10}$ and the $d_{90}$ particle size of the particles of said powder or powder mixture deviate no more than 30% from the value for the $d_{50}$ particle size of the particles of said powder or powder mixture, based on the $d_{50}$ value.

Alternatively preferred is a method according to the present invention (more preferably according to any method according to the present invention characterized herein as preferred, wherein said powder or powder mixture is a bimodal or a multimodal powder mixture. Bimodal and multimodal powder mixture allow for a high packing density which prevents entrapment of gases and the like in the melt. Especially preferred is a method according to the present invention (more preferably according to any method according to the present invention characterized herein as preferred,) wherein said powder or powder mixture is a bimodal powder mixture and the particles of a first fraction have a $d_{50}$ particle size in the range of from 1 to less than 15 µm, and the particles of a second fraction have a particle size in the range of from 15 to 100 µm. Bimodal powder mixtures for use in the present invention are for example prepared by mixing of two powders with a different grain size distribution.

On the other hand, grain size and shape of the powder or powder mixture also influences flowabilit flowability is too low, deposition of a layer of said powder or powder mixture in step (b) and especially deposition of a uniform layer, which is preferred according to the present invention, is sometimes difficult. Preferred is therefore a method according to the present invention, (more preferably according to any method according to the present invention characterized herein as preferred) wherein said powder or powder mixture has a flowability of at least 4, preferably at least 7, at a compression strength of 4 kPa (determined according to ASTM D6128). Flowability of a powder is determined according to the equation $ff_C = \sigma_1/\sigma_C$ (Flowability $ff_C$=compression stress $\sigma_1$/compression strength $\sigma_C$) as disclosed in Dietmar Schulze "Pulver und Schüttgüter", Springer-Verlag, Berlin; Auflage: 2, 2009, ISBN-10: 3540884483. Spherical particles have a better flowability than non-spherical particles. Sphericity is a measure of how spherical (round) an object is. The sphericity of a given particle is defined as the ratio of the surface area of a sphere with the same volume as the given particle) to the surface area of the particle. Preferred is a method according to the present invention (more preferably according to any method according to the present invention characterized herein as preferred) wherein the particles of said powder or powder mixture have an average sphericity of 0.8 or more, preferably of 0.9 or more. For convenience of measurement, instead of the sphericity, usually the roundness of the particles is measured. For the measurement of the roundness, two dimensional images of a large amount of particles are analyzed. Roundness R is the average ratio of the square of the circumference ($U^2$) and the area (A) of the two-dimensional image of the particles ($R=U^2/A$). Roundness can conveniently be measured by digital image processing with a CAMSIZER of the company Retsch Technology GmbH, Haan. A circle has a roundness of 12.57 and a square has a roundness of 16. Preferred is a method according to the present invention, preferably as characterized herein before as preferred, wherein the particles of said powder or powder mixture have a roundness of 16 or less, preferably of 15 or less, more preferably of 14 or less and most preferably of 13 or less.

In the method of the present invention some of the particles in the powder or powder mixture may have a different chemical composition than others. This allows for a simple preparation of said powder or powder mixture and a simple determination of the final composition of the layer by simple mixing of separate powders of different compounds. Preferred is however a method according to the present invention (more preferably according to any method according to the present invention characterized herein as preferred,) wherein at least a part and preferably all of the particles of said powder or powder mixture have the same chemical composition. This provides a melt and in turn a crystallized layer which is very homogeneous, as convection and/or diffusion over long distances are not required for intensive mixing of the components. It is preferred that at least 30% by weight, more preferably at least 60% by weight and most preferred 90% by weight of said powder or powder mixture consists of particles that have the same chemical composition.

Powders wherein at least a part or all of the particles of said powder or powder mixture have the same chemical composition can for example be prepared by spray drying of solutions containing different compounds. A further method is the use of a method where small drops of a mixture of powder, water and binder are produced and dried or hardened. The small particles produces are then dried at elevated temperatures. A further method is the precipitation of powders of mixed oxides from a solution of the constituents. The powder produced may then be processed further by spray drying or other methods. Powders with crystalline spherical particles of defined particle sizes can be produced by rapid cooling of gaseous materials.

The thickness of said layer deposited in step (b) has a strong influence on the quality of the final products and the commercial viability of the process. As mentioned above, the thickness of the layer influences the time and energy required for the melt process in step (d). Since thin layers allow for a fast melting process, they are preferred for the purposes of step (d), however, if thin layers are used, the build-up of a large number of layers may be required to produces a ceramic or glass-ceramic article. In addition, if the thickness of the layer is about the same size as the average particle diameter, not all parts of said surface may be covered by said powder or powder mixture, resulting in an uneven application of the layer and direct heating of the surface on which the powder or powder mixture is deposited in step (b). Thick layers have the opposite effects. They require long melting times and therefore have the above mentioned disadvantages concerning evaporation of part of said powder or powder mixtures. They may result in inferior physical properties as the layer may not be melted completely However, fewer layers are necessary to finish the article. A further consideration is the resolution of the process. As a rule, the total building time will decrease with increasing layer thickness. The geometric resolution of the manufactured article will decrease accordingly. In order to allow for complex geometries, the different layers will have different patterns for melting and curing the material of said powder or powder mixture. If the layer thickness is high, the pattern may change considerably between two layers, resulting in a less accurate approximation of the desired shape of the ceramic or glass-ceramic article, as the boundaries of the ceramic or glass-ceramic articles are not determined in small enough steps/increments.

Preferred is a method according to the present invention (more preferably according to any method according to the present invention characterized herein as preferred,) wherein after step (b) (if steps (a) to (e) are repeated this holds for one, two, more or all steps (b) of the complete process), but before step (d), or if step (c) is conducted before step (c), said layer deposited in step (b) has a thickness in the range of from 5 to 200 µm, preferably in the range of from 20 to 70 µm. Said layer deposited in step (b) may have the same layer thickness in every cycle or the layer thickness may be varied depending on the complexity of the patterns for melting and curing and/or the amount of geometric differences between subsequent layers. If, for instance, the patterns for melting and curing for a multitude of subsequent layers is identical, then the total building time can be reduced by increasing the layer thickness without loss of precision.

Further preferred is a method according to the present invention (more preferably according to any method according to the present invention characterized herein as preferred,) wherein during and/or after step (b) but before step (d) or (c), respectively, said layer is mechanically compressed. Mechanically compressed layers of said powder or powder mixture contain less hollow space which leads to ceramic or glass-ceramic article with less porosity. Mechanically compressed layers of said powder or powder mixture are also more uniform in thickness. A uniform thickness of said layer is important, because an adjustment of the amount of power provided by the energy beams to the thickness of the layer is difficult or at least complex and costly. Therefore, in a typical method of the present invention in step (c) and in step (d) the energy beams provide the same amount of energy to all regions to be preheated or heated. If the thickness differs throughout said layer, part of the layer may be molten completely (and even part of said surface may be molten to a large extent) while other parts of said layer may not be molten completely. This may lead to different properties in different parts of the ceramic or glass-ceramic article produced and may adversely affect physical properties like bending strength, porosity and the like.

Preferred is further a method according to the present invention (more preferably according to any method according to the present invention characterized herein as preferred,) wherein after step (b) (if steps (a) to (e) are repeated this holds for one, two, more or all steps (b) of the complete process) but before step (d), or if step (c) is conducted before step (c), said layer deposited in step (b) is leveled to a desired layer thickness. Especially preferred is a method according to the present invention as aforementioned, wherein the leveling is accomplished by positioning a leveling device at least once above the shaped body. Most preferred is a method according to the present invention (more preferably according to any method according to the present invention characterized herein as preferred,) wherein after step (b) (if steps (a) to (e) are repeated this holds for one, two, more or all steps (b) of the complete process) but before step (d), or if step (c) is conducted before step (c), said layer deposited in step (b) is leveled to a desired layer thickness, preferably by passing a leveling device over the shaped body once, two, three or more times. In any cycle of steps (a) to (e) either compression or leveling may be performed or both may be performed simultaneously or one after the other.

Tetragonal stabilised $ZrO_2$ has been established as a useful material for producing ceramic or glass-ceramic articles. When cooling a melt of $ZrO_2$ it crystallizes as cubic $ZrO_2$ and upon further cooling transforms into tetragonal $ZrO_2$ and monoclinic $ZrO_2$. It is known that the volume expansion caused by the subsequent transformations may cause damages to a ceramic or glass ceramic article. Certain oxides have been used to stabilize the cubic and/or the tetragonal phase.

Preferred is a method according to the present invention (more preferably according to any method according to the present invention characterized herein as preferred,) wherein said powder or powder mixture comprises $ZrO_2$ and at least one component selected from the group consisting of MgO, $Y_2O_3$, CaO and $CeO_2$. These oxides stabilize the tetragonal phase of $ZrO_2$, thereby reducing the volume expansion of the $ZrO_2$ which reduces mechanical stress, cracks, fissures and other damages in the ceramic or glass ceramic article.

Especially preferred is a method according to the present invention (more preferably according to any method according to the present invention characterized herein as preferred,) wherein said powder or powder mixture comprises $ZrO_2$ and at least one component selected from the group consisting of $Y_2O_3$, $CeO_2$ and MgO and wherein the amount of the component or components selected from said group is preferably sufficient to stabilize at least 50% by volume, preferably at least 75% by volume of the $ZrO_2$ in the final article in the tetragonal form and wherein, if selected, in particular if selected as sole component from the group, the amount of $Y_2O_3$ is preferably in the range of 1 to 7 percent by weight, the amount of $CeO_2$ is preferably in the range of 5 to 15 percent by weight and the amount of MgO is preferably in the range of 3 to 10 percent by weight based on the amount of $ZrO_2$. Further preferred is a method according to the present invention (more preferably according to any method according to the present invention characterized herein as preferred,) wherein in said ceramic or glass-ceramic article at least 50 percent by volume and preferably at least 75 percent by volume of the total volume of $ZrO_2$ in the article is tetragonal stabilized, doped $ZrO_2$.

Preferred is a method according to the present invention, wherein, if steps (a) to (e) are not repeated, after step (e), or if steps (a) to (e) are repeated, after the final repetition of steps (a) to (e), a treatment for improving bending strength is performed. The treatment for improving bending strength is preferably a surface roughness reducing step, preferably selected from the group consisting of machining (polishing, grinding, sand-blasting) and surface coating (veneering etc).

Preferred is a method according to the present invention (more preferably according to any method according to the present invention characterized herein as preferred,) wherein, if steps (a) to (e) are not repeated, after step (e), or if steps (a) to (e) are repeated, after the final repetition of steps (a) to (e), a thermal treatment or glass-infiltration of the intermediate product as obtained after final step (e) is performed. The thermal treatment preferably is an "annealing treatment" (i.e. a treatment at a temperature below sintering temperature).

A thermal aftertreatment of said intermediate product can lead to alleviation of stress by means of superplasticity (as described above) or sintering or otherwise. This process can repair some of the damages incurred by mechanical stress through cooling. If a thermal after treatment (after final step (e)) is performed, preheating step (c) can generally be omitted without causing inacceptable damages. Additionally, thermal aftertreatment of said intermediate product can lead to improvement of bending strength, fracture toughness and other physical properties through crystallization of amorphous phases.

An aspect of the present invention relates to a method according to the present invention, preferably according to any method according to the present invention characterized herein as preferred,) of producing a ceramic or glass-ceramic article comprising the steps of:

(a) providing a powder or a powder mixture comprising ceramic or glass-ceramic material, wherein said powder or powder mixture preferably comprises components that form an eutectic system with each other, (b) depositing a layer of said powder or powder mixture on a surface, (c) preheating of at least one region of said layer to a preheating temperature such that no part of said ceramic or glass-ceramic material in said at least one region is melted, (d) heating of at least one region of said layer by means of an energy beam or a plurality of energy beams to a maximum temperature such that at least a part of said ceramic or glass-ceramic material in said at least one region is melted, wherein the maximum temperature is higher than the preheating temperature, (e) cooling of said at least one region of said layer so that at least part of the material melted in step (d) is solidified, such that the layer is joined with said surface, (f) repeating of steps (a) to (e), whereby the surface of the layer produced by each foregoing series of steps (a) to (e) is used in step (b) of the repetition as surface for the following layer.

Preferred is a method according to this aspect of the present invention, wherein after the final repetition of steps (a) to (e) a thermal treatment or glass-infiltration of the intermediate product obtained is performed, preferably as described above.

Statements made above regarding preferred embodiments of methods of the present invention apply also to this aspect of the invention.

Preferred is a method according to the present invention, preferably as characterized herein before, (more preferably according to any method according to the present invention characterized herein as preferred,) wherein, if steps (a) to (e) are not repeated, after step (e), or if steps (a) to (e) are repeated, after the final repetition of steps (a) to (e), a glass-infiltration of the intermediate product obtained is performed at a temperature in the range of from 650° C. to 1200° C., preferably in the range of from 850° C. to 1000° C.

Particularly preferred is a method according to the present invention (more preferably according to any method according to the present invention characterized herein as preferred,) wherein, if steps (a) to (e) are not repeated, after step (e), or if steps (a) to (e) are repeated, after the final repetition of steps (a) to (e), a glass-infiltration of the intermediate product obtained is performed under process conditions which are selected such that less than 5% by weight of the intermediate product is dissolved in the glass used for glass infiltration. In particular, glass infiltration temperature and time are carefully controlled. The amount of the material of the intermediate product dissolved in the glass used for glass infiltration is for the purposes of the present invention measured by energy-dispersive X-ray spectroscopy.

Likewise preferred is a method according to the present invention, (more preferably according to any method according to the present invention characterized herein as preferred,) wherein, if steps (a) to (e) are not repeated, after step (e), or if steps (a) to (e) are repeated, after the final repetition of steps (a) to (e), a glass-infiltration of the intermediate product obtained is performed under conditions and, in particular, at a temperature and for a time interval such that more than 60%, preferably more that 80% and most preferably more than 95% of the pores of the intermediate product are closed. High effective porosity (also called open porosity) may adversely affect bending strength, fracture toughness and other physical properties of the ceramic or glass-ceramic articles produced. It may also adversely affect chemical resistance, especially chemical solubility. It is therefore usually desirable to produce ceramic or glass-ceramic articles with as few and as small pores as possible. Porosity and effective porosity can be measured by image analysis of cross-sections of the ceramic or glass-ceramic articles produced and other methods. Effective porosity can also be measured by the water saturation method, mercury intrusion porosimetry and other methods. For the purposes of the present invention effective porosity is measured according to the water saturation method as disclosed in the norm ISO/FDIS 18754.

Further preferred is a method according to the present invention, (more preferably according to any method according to the present invention characterized herein as preferred,) wherein, if steps (a) to (e) are not repeated, after step (e), or if steps (a) to (e) are repeated, after the final repetition of steps (a) to (e) a glass-infiltration of the intermediate product obtained is performed under conditions, in particular at a temperature and for a time interval such that the bending strength of the ceramic or glass ceramic article has a higher value after glass infiltration than the intermediate product. Further preferred is a method according to the present invention, (more preferably according to any method according to the present invention characterized herein as preferred,), in particular, when air sensitive components are comprised in the intermediate product (see above) or in the glass used for glass infiltration, wherein the glass infiltration is performed under inert (protective) gas or in a vacuum. The latter method is especially preferred, as it allows for a very significant reduction of the effective porosity.

Further preferred is a method according to the present invention (more preferably according to any method according to the present invention characterized herein as preferred,) wherein, if steps (a) to (e) are not repeated, after step (e), or if steps (a) to (e) are repeated, after the final repetition of steps (a) to (e) a glass-infiltration of the intermediate product obtained is performed with a glass which comprises or consists of at least one compound selected from but favorably all compounds of the group consisting of $ZrO_2$, $SiO_2$, $B_2O_3$, $Al_2O_3$, $Li_2O$ and $CaO$.

Particularly preferred is a method according to the present invention (more preferably according to any method according to the present invention characterized herein as preferred,) wherein, if steps (a) to (e) are not repeated, after step (e), or if steps (a) to (e) are repeated, after the final repetition of steps (a) to (e) a glass-infiltration of the intermediate product obtained is performed with a glass consisting of 15 to 25 percent by weight $SiO_2$,
20 to 30 percent by weight $B_2O_3$,
30 to 40 percent by weight $Al_2O_3$,
10 to 20 percent by weight $Li_2O$,
2.5 to 7.5 percent by weight $CaO$,
0 to 3 percent by weight $ZrO_2$,
and optionally further oxides,
wherein all percent by weight data are based on the total weight of the glass.

Further preferred is a method according to the present invention (more preferably according to any method according to the present invention characterized herein as preferred,) wherein, if steps (a) to (e) are not repeated, after step (e), or if steps (a) to (e) are repeated, after the final repetition of steps (a) to (e) a glass-infiltration of the intermediate product obtained is performed, such that said ceramic or glass-ceramic article after glass infiltration has a bending strength of at least 25 MPa, preferably of at least 250 MPa and more preferably of at least 500 MPa. For the purpose of the present invention the bending strength is measured according to the norm DIN EN 843-1.

In methods according to the present invention, preferably according to any method according to the present invention characterized herein as preferred, said ceramic or glass-ceramic article is produced on a surface which is part of a substrate. Preferred is a method, wherein said ceramic or glass-ceramic article is produced on a substrate comprising a support means and/or a connector (e.g. connecting the support means to the body of the apparatus used). Further preferred is a method according to the present invention, wherein the support means or the connector has a predetermined breaking point to facilitate the separation of said ceramic or glass-ceramic article.

In case the substrate is used either with support means or a connector, it is preferred that the surface according to step (b) is part of the support means or the connector. In case the substrate is used with support means and a connector, the surface according to step (b) is preferably part of the support means.

Further preferred is a method according to the present invention, wherein the process is controlled by a computer and/or a control unit. Said energy beam used for heating in step (d)—and, if applicable an energy beam used for preheating in step (c)—may be controlled by a computer using data attained e.g. by sampling a three-dimensional shape (of a sample) to be reproduced or otherwise. In such a case direction of said energy beam or at least one of said plurality of energy beams in a predetermined exposure pattern as represented by the data is used to shape the ceramic or glass-ceramic article in a layer by layer fashion. Further preferred is therefore a method according to the present invention, preferably as characterized herein before (more preferably according to any method according to the present invention characterized herein as preferred,) wherein the energy beam, in particular its intensity (power), focus, pathway, speed and/or the like is controlled and guided by a computer system. This allows a fast processing speed and a fast production of the ceramic and glass articles. It is preferred that said computer system uses data from sampling (sample scanning), a CAD/CAM system or the like. As to the control of an energy beam in a SLS by a computer see U.S. Pat. No. 5,508,489, already discussed above. A similar approach can be used in the method of the present invention.

Preferred is a method according to the present invention, (more preferably according to any method according to the present invention characterized herein as preferred,) wherein the temperature of the surface of said layer is at least once measured by a pyrometer. Preferred is a method according to the present invention (preferably according to any method according to the present invention characterized herein as preferred,) wherein the temperature of the surface of said layer is at least once measured (preferably by means of a pyrometer) during step (c). Further preferred is a method according to the present invention, wherein the data corresponding to the measured temperature are used for process monitoring and/or process control, preferably using a computer (see above). By this method heating can be stopped once the powder or powder mixture has the desired temperature. Overheating and not sufficient heating can be avoided. The processing speed is accelerated and the properties or the ceramic and glass-ceramic articles are improved.

Preferred is a method according to the present invention, (more preferably according to any method according to the present invention characterized herein as preferred,) wherein the average grain size in said produced ceramic or glass-ceramic article produced is 10 µm or smaller, preferably 2.5 µm or smaller. Throughout the present document grain sizes in solid bodies are measured by the linear intercept method according to DIN EN 623-3. Herein preferred is a method wherein said ceramic or glass-ceramic article produced contains grains of optionally doped $ZrO_2$ and wherein the average grain size of said grains of $ZrO_2$ is less than 0.5 µm.

The present invention provides a free form process for the production of ceramic or glass-ceramic articles with superior properties, like bending strength, hardness and smoothness of the surface, fracture toughness, fracture strength, biocompatibility, low overall pore volume and the like. Preferred is a method according to the present invention (more preferably according to any method according to the present invention characterized herein as preferred,) wherein said ceramic or glass-ceramic article has a bending strength of at least 25 MPa, preferably of at least 250 MPa and more preferably of at least 500 MPa. Further preferred is a method according to the present invention, (more preferably according to any method according to the present invention characterized herein as preferred,) wherein the fracture toughness of said ceramic or glass-ceramic article is at least 4 $MPa*m^{1/2}$, preferably at least 6 $MPa*m^{1/2}$. For the purposes of the present invention, the fracture toughness is measured according to the method described in K. M. Liang et al, "Evaluation by indentation of fracture toughness of ceramic materials", Journal of Materials Science 25 (1990) 207-214, item 3.2 and the literature cited therein.

Preferred is also a method according to the present invention, (more preferably according to any method according to the present invention characterized herein as preferred,) wherein the fraction of the glass phase in said ceramic or glass-ceramic article is 40 percent by volume or less, preferably 10 percent by volume or less. For the purposes of the present invention, the fraction of the glass phase is determined by powder diffraction (XRD). Further preferred is a method according to the present invention (more preferably according to any method according to the present invention characterized herein as preferred,) wherein the porosity of said ceramic or glass-ceramic article produced is no more than 30 percent by volume, preferably no more than 5 percent by volume.

The method according to the present invention provides superior ceramic or glass-ceramic articles by rapid production of prototypes in a timely and cost effective manner. Preferred is a method according to the present invention, (more preferably according to any method according to the present invention characterized herein as preferred,) wherein a plurality of articles is produced in parallel. In such a process, a plurality of surfaces according to step (b) are preferably arranged in an array format. Preferably all surfaces are in the same (horizontal) plane. In such an arrangement, layers of said powder or powder mixture is preferably deposited on all surfaces in one production step and heating is provided to all layers of said powder or powder material in said plain. Heating of the plurality of layers (in the same place) may be conducted simultaneously, serially or intermittently. Thereby a single apparatus is able to produce a plurality of articles in little more time (cycle time) than is necessary for the production of a single article. This approach makes the present invention more cost effective than conventional subtractive methods, in which an apparatus may only produce a single article at a given time. The present invention allows for the cost effective production of small batch series of identical ceramic and/or glass-ceramic articles, for example for the ceramic industry, and it allows for the production of individual articles that have the same composition, a similar size, but a different shape. As an example for the latter, dental articles such as a crown, a bridge, an inlay, an onlay or abutments, can be named, but also articles for the electronic industry, where, for example, similar but not identical articles have to be produced to be able to analyze the change of a property of the articles corresponding to a change in the shape.

In a preferred method according to the present invention (more preferably according to any method according to the present invention characterized herein as preferred,) said ceramic or glass-ceramic article is a dental article, in particular a dental restoration or frame. In a particularly preferred method according to the present invention, (more preferably according to any method according to the present invention characterized herein as preferred,) said ceramic or glass-ceramic dental article is a crown, a bridge, an inlay, an onlay or an abutment. Particularly preferred is a method according to the present invention (more preferably according to any method according to the present invention characterized herein as preferred,) wherein said ceramic or glass-ceramic (preferably dental) article is tooth-colored.

A further aspect of the present invention relates to a method of producing a ceramic or glass-ceramic article comprising the steps of:

(a) providing a powder or a powder mixture of ceramic or glass-ceramic material, (b) depositing a layer of said powder or powder mixture on a surface, (c) preheating of at least one region of said layer to a preheating temperature such that no part of said powder or powder mixture in said at least one region is melted, (d) heating at least one region preheated in step (c) by means of an energy beam or a plurality of energy beams to a maximum temperature such that at least a part of said powder or powder mixture in said at least one region is melted, (e) cooling said at least one region heated in step (d) so that at least part of the material melted in step (d) is solidified, such that the layer is joined with said surface, wherein said preheating temperature is in the range of from 40% to 99%, preferably in the range of from 60% to 95% of the minimum temperature ("liquidification temperature") at which a crystalline part of said ceramic or glass-ceramic material in said at least one region is melted, wherein said powder or powder mixture comprises $ZrO_2$, $Al_2O_3$ and at least one component selected from the group consisting of $Y_2O_3$, $CeO_2$ and MgO, wherein the mixing ratio by weight of $ZrO_2$ to $Al_2O_3$ is in the range of from 1:4 to 4:1, preferably in the range of from 3:7 to 7:3, wherein, if selected, in particular if selected as sole component from the group, the amount of $Y_2O_3$ is in the range of 1 to 7 percent by weight, the amount of $CeO_2$ is in the range of 5 to 15 percent by weight and the amount of MgO is in the range of 3 to 10 percent by weight based on the overall amount of $ZrO_2$, and wherein in said ceramic or glass-ceramic article at least 50 percent by volume and preferably at least 75 percent by volume of the total volume of $ZrO_2$ in the article is tetragonal stabilized, doped $ZrO_2$, and wherein the average particle grain size in the article is 10 µm or smaller, preferably 2.5 µm or smaller.

Statements made above regarding preferred embodiments of methods of the present invention apply also to this aspect of the invention.

A further aspect of the present invention relates to a method of producing a ceramic or glass-ceramic article comprising the steps of:

(a) providing a powder or a powder mixture of ceramic or glass-ceramic material, (b) depositing a layer of said powder or powder mixture on a surface, (c) preheating of at least one region of said layer to a preheating temperature such that no part of said powder or powder mixture in said at least one region is melted, (d) heating at least one region preheated in step (c) by means of an energy beam or a plurality of energy beams to a maximum temperature such that at least a part of said powder or powder mixture in said at least one region is melted, (e) cooling said at least one region heated in step (d) so that at least part of the material melted in step (d) is solidified, such that the layer is joined with said surface, wherein said preheating temperature is in the range of from 40% to 99%, preferably in the range of from 60% to 95% of the minimum temperature ("liquidification temperature") in Kelvin (K) at which a crystalline part of said ceramic or glass-ceramic material in said at least one region is melted and wherein at least 70 percent by weight of said powder or powder mixture consists of components that form an eutectic system with each other and wherein for each component of said eutectic system the, based on the weight of the eutectic system in the powder or powder mixture, of the component in said powder or powder mixture is at least 70% of the fraction by weight of the same component in the eutectic mixture of said eutectic system and wherein at least 70 percent by weight said powder or powder mixture consists of one or more compounds selected from the group consisting of $Al_2O_3$, $ZrO_2$, $Y_2O_3$, $Na_2O$, $Nb_2O_5$, $La_2O_3$, CaO, SrO, $CeO_2$, MgO, $SiO_2$, $TiO_2$, $Cr_2O_3$, CuO, $Eu_2O_3$, $Er_2O_3$, CoO, $Gd_2O_3$, the mixed oxides thereof, SiC, TiC, $Si_3N_4$ and AlN, and wherein the average particle grain size in the article is 10 µm or smaller, preferably 2.5 µm or smaller.

Statements made above regarding preferred embodiments of methods of the present invention apply also to this aspect of the invention.

A further aspect of the present invention is a method of producing a ceramic or glass-ceramic article comprising the steps of:

(a) providing a powder or a powder mixture of ceramic or glass-ceramic material, (b) depositing a layer of said powder or powder mixture on a surface, (c) preheating of at least one region of said layer to a preheating temperature such that no part of said powder or powder mixture in said at least one region is melted, (d) heating at least one region of said layer by means of an energy beam or a plurality of energy beams to a maximum temperature such that at least a part of said powder or powder mixture in said at least one region is melted, (e) cooling said at least one region of said layer so that at least part of the material melted in step (d) is solidified, such that the layer is joined with said surface, wherein said preheating temperature is in the range of from 40% to 99%, preferably in the range of from 60% to 95% of the minimum temperature ("liquidification temperature") in Kelvin (K) at which a crystalline part of said ceramic or glass-ceramic material in said at least one region is melted and wherein at least 70 percent by weight of said powder or powder mixture consists of one or more compounds selected from the group consisting of $Al_2O_3$, $ZrO_2$, $Y_2O_3$, $Na_2O$, $Nb_2O_5$, $La_2O_3$, CaO, SrO, $CeO_2$, MgO, $SiO_2$, $TiO_2$, $Cr_2O_3$, CuO, $Eu_2O_3$, $Er_2O_3$, CoO, $Gd_2O_3$, the mixed oxides thereof, SiC, TiC, $Si_3N_4$ and AlN, and wherein said powder or powder mixture consists of particles with a $d_{50}$ particle size in the range of from 1 to 100 µm, preferably in the range of from 15 to 70 µm, and wherein the method further comprises the following separate step:

preheating of said powder or powder mixture before step (b) to a powder preheating temperature, such that no part of said ceramic or glass-ceramic material is melted and such that said powder or powder mixture preferably has a powder preheating temperature (temperature when being deposited on said surface, see definition above) in the range of from 40% to 70% of the melting temperature in Kelvin of said powder or powder mixture.

Preferably, said powder or powder mixture is preheated before step (b) by means of microwave radiation or infrared radiation or a radiant heater.

In a particularly preferred embodiment of the present invention the powder preheating temperature is higher than the temperature of any region of said surface in step (b), and if the method is performed in a chamber, is also higher than the temperature of the chamber.

Statements made above regarding preferred embodiments of methods of the present invention apply also to this aspect of the invention.

A further aspect of the present invention relates to a method of producing a ceramic or glass-ceramic article comprising the steps of:

(a) providing a powder or a powder mixture of ceramic or glass-ceramic material, (b) depositing a layer of said powder or powder mixture on a surface, (d) heating at least one region of said layer by means of an energy eam or a plurality of energy beams to a maximum temperature such that at least a part of said powder or powder mixture in said at least one region is melted, (e) cooling said at least one region of said layer so that at least part of the material melted in step (d) is solidified, such that the layer is joined with said surface, wherein said powder or powder mixture comprises $ZrO_2$, $Al_2O_3$ and at least one component selected from the group consisting of $Y_2O_3$, $CeO_2$ and MgO and wherein the mixing ratio by weight of $ZrO_2$ to $Al_2O_3$ is in the range of from 1:4 to 4:1, preferably in the range of from 3:7 to 7:3, wherein, if selected, in particular if selected as sole component from the group, the amount of $Y_2O_3$ is in the range of 1 to 7 percent by weight, the amount of $CeO_2$ is in the range of 5 to 15 percent by weight and the amount of MgO is in the range of 3 to 10 percent by weight based on the overall amount of $ZrO_2$, and wherein in said ceramic or glass-ceramic article at least 50 percent by volume and preferably at least 75 percent by volume of the total volume of $ZrO_2$ in the article is tetragonal stabilized, doped $ZrO_2$.

Statements made above regarding preferred embodiments of methods of the present invention apply also to this aspect of the invention.

A further aspect of the present invention is a method of producing a ceramic or glass-ceramic article comprising the steps of:

(a) providing a powder or a powder mixture of ceramic or glass-ceramic material, (b) depositing a layer of said powder or powder mixture on a surface, (d) heating at least one region of said layer by means of an energy beam or a plurality of energy beams to a maximum temperature such that at least a part of said powder or powder mixture in said at least one region is melted, (e) cooling said at least one region of said layer so that at least part of the material melted in step (d) is solidified, such that the layer is joined with said surface, wherein at least 70 percent by weight of said powder or powder mixture consists of components that form an eutectic system with each other and wherein for each component of said eutectic system the fraction by weight of the component in said powder or powder mixture, based on the weight of the eutectic system in the powder or powder mixture, is at least 25%, preferably at least 50%, especially preferred at least 70% and most preferred at least 90% of the fraction by weight of the same component in the eutectic mixture of said eutectic system, and wherein said powder or powder mixture consists of particles with a $d_{50}$ particle size in the range of from 1 to 100 μm, preferably in the range of from 15 to 70 μm.

Statements made above regarding preferred embodiments of methods of the present invention apply also to this aspect of the invention.

In a preferred method of producing a ceramic or glass-ceramic article according to the present invention in a first step (b) a first layer of said powder or powder mixture (as described above, preferably according to any method according to the present invention characterized herein as preferred) is deposited on the surface of a substrate (typically in the form of a substrate plate). After first step (e) the first layer of said powder or powder mixture is joined with said surface of the substrate.

In such a preferred method the substrate (typically a substrate plate) preferably has a thermal expansion coefficient which is sufficiently close to the thermal expansion coefficient of the ceramic or glass-ceramic article produced that no significant mechanical stress is caused during the layerwise build-up. Preferably, the difference of the thermal expansion coefficients of (i) the substrate and (ii) the produced article is less than $2*10^{-6}K^{-1}$, preferably less than $1*10^{-6}K^{-1}$ in the temperature range of from 25° C. to 1500° C. By using corresponding pairs of substrate and powder material, mechanical stress can be avoided as well as stress-induced cracks or fissures.

In a preferred method of producing a ceramic or glass-ceramic article according to the present invention the produced ceramic or glass-ceramic article comprises support elements joined to the substrate surface, wherein the support elements define predetermined breaking points for separating the produced article from the substrate surface. When producing such an article the support elements are build-up first, starting with a first layer of powder or a powder mixture that is joined to the substrate surface.

A further aspect of the present invention is a powder or powder mixture as described herein. Preferred is a powder or powder mixture comprising or consisting of $Al_2O_3$, $ZrO_2$, and at least one component selected from the group consisting of $Y_2O_3$, $CeO_2$, MgO, wherein at least 50 percent by weight, preferably at least 70 percent by weight of said powder or powder mixture consists of $Al_2O_3$ and $ZrO_2$, wherein the mixing ratio by weight of $ZrO_2$ to $Al_2O_3$ is in the range of from 3:7 to 7:3, wherein said powder or powder mixture consists of particles with a $d_{50}$ particle size in the range of from 1 to 100 μm, preferably in the range of from 15 to 70 μm, wherein the particles of said powder or powder mixture have a roundness of 16 or less, preferably of 15 or less, more preferably of 14 or less and most preferably of 13 or less and wherein said powder or powder mixture has a flowability of at least 4, preferably at least 7. Preferred is a powder or powder mixture as described herein, (a) comprising $Y_2O_3$ in an amount in the range of 1 to 7 percent by weight, (b) comprising $CeO_2$ in an amount in the range of 5 to 15 percent by weight, or (c) comprising MgO in an amount in the range of 3 to 10 percent by weight in each case based on the amount of $ZrO_2$.

Especially preferred is a powder or powder mixture comprising or consisting of $Al_2O_3$, $ZrO_2$, and at least one component selected from the group consisting of $Y_2O_3$, $CeO_2$, MgO, wherein at least 50 percent by weight of said powder or powder mixture consists of $Al_2O_3$ and $ZrO_2$, wherein the mixing ratio by weight of $ZrO_2$ to $Al_2O_3$ is in the range of from 3:7 to 7:3, wherein, if selected, in particular if selected as sole component from the group, the amount of $Y_2O_3$ is preferably in the range of 1 to 7 percent by weight, the amount of $CeO_2$ is preferably in the range of 5 to 15 percent by weight and the amount of MgO is preferably in the range of 3 to 10 percent by weight based on the amount of $ZrO_2$, wherein said powder or powder mixture consists of particles with a $d_{50}$ particle size in the range of from 1 to 100 μm, wherein the particles of said powder or powder mixture have a roundness of 14 or less and wherein said powder or powder mixture has a flowability of at least 4.

Statements made above regarding preferred embodiments of methods of the present invention apply also to this aspect of the invention in so far as they concern powder or powder mixtures.

A further aspect of the present invention relates to a ceramic or glass-ceramic article producible by a method according to the present invention, more preferably producible according to any method according to the present invention characterized herein as preferred. Particularly preferred is a ceramic or glass-ceramic article according to the present invention (more preferably prepared or producible according to any method according to the present invention characterized herein as preferred,) wherein the article is a dental article, particularly a dental restoration or frame, e.g. a dental crown, a bridge, an inlay, an onlay or an abutment. Further preferred is a ceramic or glass-ceramic article according to the present invention wherein the preferably dental article is tooth-colored.

As mentioned above, the present invention allows the production of ceramic and glass-ceramic articles, wherein the material of the article has a small grain size. Such articles have superior properties over ceramic or glass-ceramic articles with a large grain size. Preferred is a ceramic or glass-ceramic article according to the present invention, (more preferably having features characterized herein as preferred,) wherein the average particle grain size in the article is 10 μm or smaller, preferably 2.5 μm or smaller. Particularly preferred is a ceramic or glass-ceramic article of the present invention which contains grains of $ZrO_2$, wherein the average grain size of said grains of $ZrO_2$ is less than 0.5 µm.

Preferred is a ceramic or glass-ceramic article according to the present invention, (preferably a ceramic or glass-ceramic article according to the present invention characterized herein as preferred,) which comprises components that form an eutectic mixture which each other.

Preferred is a ceramic or glass-ceramic article according to the present invention, (more preferably a ceramic or glass-ceramic article according to the present invention characterized herein as preferred,) wherein said article has a bending strength of at least 25 MPa, preferably of at least 250 MPa and more preferably of at least 500 MPa. Further preferred is a ceramic or glass-ceramic article according to the present invention, (more preferably a ceramic or glass-ceramic article according to the present invention characterized herein as preferred,) wherein the fracture toughness of the article is at least 4 MPa*m$^{1/2}$, preferably at least 6 MPa*m$^{1/2}$.

Preferred is a ceramic or glass-ceramic article according to the present invention (preferably a ceramic or glass-ceramic article according to the present invention characterized herein as preferred,) comprising or consisting of material that has an m value (see the above discussion of superplasticity) maximum in the temperature range of from 1350° C. to 1500° C. of at least 0.5, preferably of at least 0.75.

Further preferred is a ceramic or glass-ceramic article according to the present invention (preferably a ceramic or glass-ceramic article according to the present invention characterized herein as preferred,) that is biocompatible according to ISO 10993-1 and ISO 7405, bioinert or bioactive.

Further preferred is a ceramic or glass-ceramic article according to the present invention (preferably a ceramic or glass-ceramic article according to the present invention characterized herein as preferred,) wherein the chemical solubility is 100 µg/cm$^{-2}$ or less, preferably 20 µg/cm$^{-2}$ or less according to DIN EN ISO 6872:1998.

Preferred is also a ceramic or glass-ceramic article according to the present invention, (preferably a ceramic or glass-ceramic article according to the present invention characterized herein as preferred,) wherein the fraction of the glass phase in the article is 40 percent by volume or less, preferably 10 percent by volume or less.

Further preferred is a ceramic or glass-ceramic article according to the present invention, (preferably a ceramic or glass-ceramic article according to the present invention characterized herein as preferred,) wherein the porosity of the article is no more than 30 percent by volume, preferably no more than 5 percent by volume.

A further aspect of the present invention relates to the use of a ceramic or glass-ceramic article according to the present invention, (preferably a ceramic or glass-ceramic article according to the present invention characterized herein as preferred,) as a dental article, in particular as a dental restoration (e.g. bridge, crown, inlay, onlay, abutment) or frame, or in the electronic industry.

Still a further aspect of the present invention is an apparatus for producing a ceramic or glass-ceramic article, wherein the apparatus comprises at least one energy beam source for providing at least two energy beams operable independently of each other,
at least one storage container for a powder or a powder mixture,
a substrate for depositing a layer of said powder or a powder mixture,
a powder deposition device for depositing a layer or layers of said powder or powder mixture on the substrate,
means to direct the energy beams onto the surface or surfaces of the layer or layers of the powder or powder mixture.

Preferred is an apparatus according to the present invention, preferably as described herein before, wherein the container comprises a powder or a powder mixture, which comprises components that form an eutectic system with each other.

In order to preserve energy and to prevent rapid cooling of the melt, heat transmission from said layer deposited in step (b) and heated in step (d) and/or said surface and/or the intermediate article already produced is preferably reduced by isolation of said layer, said surface and/or said intermediate article from the environment and/or the surrounding apparatus by an isolating material. Thus, preferred is an apparatus according to the present invention, comprising insulation material with a heat transfer coefficient of 20 W/(m$^2$K) or less, preferably 10 W/(m$^2$K) or less for at least a partly insulation of said layer deposited in step (b) and heated in step (d). Further preferred is an apparatus according to the present invention, preferably as described herein before, comprising insulation material with a heat transfer coefficient of 20 W/(m$^2$K) or less, preferably 10 W/(m$^2$K) or less for at least a partly insulation of said surface. Still further preferred is an apparatus according to the present invention, preferably as described herein before, comprising insulation material with a heat transfer coefficient of 20 W/(m$^2$K) or less, preferably 10 W/(m$^2$K) or less for at least a partly insulation of said intermediate article. Most preferred is an apparatus according to the present invention, preferably as described herein before, comprising insulation material with a heat transfer coefficient of 20 W/(m$^2$K) or less, preferably 10 W/(m$^2$K) or less for at least a partly insulation of said layer deposited in step (b) and heated in step (d), said surface and said intermediate article.

Further preferred is an apparatus according to the present invention, (and especially preferred according to any apparatus described herein as preferred) wherein the apparatus comprises a pyrometer for measuring the temperature on the surface of the layer and/or a computer for the control of the production process.

An apparatus that can be easily adapted for the use in the present invention is disclosed in EP 1 234 625 A1. Especially the method for distribution of the metallic material powder over the building platform or the building space by means of a leveling device disclosed in EP 1 234 625 A1, paragraphs [0035] to [0054] and FIGS. 2 to 7 can be used analogously in the method according to the present invention. Preferred is therefore an apparatus according to the present invention which comprises an applicator unit (deposition device) for depositing a layer of said powder or powder mixture on said surface in step (b) and at least one leveling device for leveling the surface of the layer deposited in step (b). Preferred is further an apparatus according to the present invention, comprising at least one leveling device, wherein at least one leveling device comprises individual elements that pull off or brush off the powder layer down to the desired layer thickness. The individual elements are preferably brushes, comprising or consisting of carbon fiber or fibers comprising or consisting of metal oxides. Since carbon fibers easily oxidize at high temperatures in an oxygen containing gas like air, fibers comprising or consisting of metal oxides are preferred. Most preferred are brushes consisting of aluminum oxide.

A further aspect of the present invention is a ceramic or glass-ceramic article comprising
- a set of adjacent, joined layers of ceramic or glass-ceramic material, wherein said layers have a thickness in the range of from 5 to 200 μm,
and/or
- a set of adjacent, joined tracks of ceramic or glass-ceramic material, wherein said article has a bending strength of at least 25 MPa, preferably of at least 250 MPa and more preferably of at least 500 MPa.

Statements made above regarding preferred embodiments of articles of the present invention apply also to this aspect of the invention.

Preferred is a ceramic or glass-ceramic article according to the present invention, preferably as described herein before, wherein said layers have a thickness in the range of from 20 to 70 μm.

Further preferred is a ceramic or glass-ceramic article according to the present invention, preferably as described herein before, with a bending strength of at least 25 MPa, preferably of at least 250 MPa and more preferably of at least 500 MPa. Preferred is also a ceramic or glass-ceramic article according to the present invention, preferably as described herein before, wherein the fracture toughness of the article is at least 4 $MPa*m^{1/2}$, preferably at least 6 $MPa*m^{1/2}$.

Further preferred is a ceramic or glass-ceramic article according to the present invention, preferably as described herein before, wherein the average grain size in the article is 10 μm or smaller, preferably 2.5 μm or smaller.

Further preferred is a ceramic or glass-ceramic article according to the present invention, (and especially preferred according to any ceramic or glass-ceramic article described herein as preferred) wherein the article comprises a glass phase, the fraction of the glass phase in the article being no more than 40 percent by volume, preferably no more than 10 percent by volume.

Further preferred is a ceramic or glass-ceramic article according to the present invention, preferably as described herein before, (and especially preferred a ceramic or glass-ceramic article described herein as preferred) which comprises or consists of compounds selected from the group consisting of $SiO_2$, $B_2O_3$, $Al_2O_3$, $Li_2O$, $ZrO_2$ and CaO. Herein especially preferred is a ceramic or glass-ceramic article, wherein said glass phase, consists of
- 15 to 25 percent by weight $SiO_2$,
- 20 to 30 percent by weight $B_2O_3$,
- 30 to 40 percent by weight $Al_2O_3$,
- 10 to 20 percent by weight $Li_2O$,
- 2.5 to 7.5 percent by weight CaO,
- 0 to 3 percent by weight $ZrO_2$
- and optionally further oxides, wherein all percent by weight data are based on the total weight of the glass.

Further preferred is a ceramic or glass-ceramic article according to the present invention, (especially preferred according to any ceramic or glass-ceramic article described herein as preferred) wherein the porosity of the article is no more than 30 percent by volume, preferably no more than 5 percent by volume.

A further aspect of the present invention is a ceramic or glass-ceramic article, comprising
- a set of adjacent, joined layers of ceramic or glass-ceramic material, wherein said layers have a thickness in the range of from 5 to 200 μm,
and/or
- a set of adjacent, joined tracks of ceramic or glass-ceramic material, wherein said ceramic or glass-ceramic material comprises components that form an eutectic system with each other.

Statements made above regarding preferred embodiments of articles of the present invention apply also to this aspect of the invention.

Preferred is a ceramic or glass-ceramic article, preferably as described herein before, wherein at least 50 percent by weight, preferably at least 70 percent by weight of said ceramic or glass-ceramic material consist of components that form an eutectic system with each other. Herein further preferred is a ceramic or glass-ceramic article wherein said ceramic or glass-ceramic material comprises components that form an eutectic system with each other, and wherein for each component of said eutectic system the fraction by weight of the component in said ceramic or glass-ceramic material, based on the weight of the eutectic system in the powder or powder mixture, is at least 25%, preferably at least 50%, especially preferred at least 70% and most preferred at least 90% of the fraction by weight of the same component in the eutectic mixture of said eutectic system.

Preferred is a ceramic or glass-ceramic article according to the present invention, preferably as described herein before, (and especially preferred according to any ceramic or glass-ceramic article described herein as preferred) comprising one or more compounds selected from the group consisting of $Al_2O_3$, $ZrO_2$, $Y_2O_3$, $Na_2O$, $Nb_2O_5$, $La_2O_3$, CaO, SrO, $CeO_2$, MgO, $SiO_2$, $TiO_2$, $Cr_2O_3$, CuO, $Eu_2O_3$, $Er_2O_3$, CoO, $Gd_2O_3$ the mixed oxides thereof (especially $MgAl_2O_4$, $Y_3Al_5O_{12}$, $Er_3Al_5O_{12}$, $NiAl_2O_4$, $LaAlO_3$ and $La_2ZrO_7$), SiC, TiC, $Si_3N_4$ and AlN. Hereby preferred is a ceramic or glass-ceramic article, wherein at least 50 percent by weight, preferably at least 70 percent by weight of said article consist of one or more compounds selected from the group consisting of $Al_2O_3$, $ZrO_2$, $Y_2O_3$, $Na_2O$, $Nb_2O_5$, $La_2O_3$, CaO, SrO, $CeO_2$, MgO, $SiO_2$, $TiO_2$, $Cr_2O_3$, CuO, $Eu_2O_3$, $Er_2O_3$, CoO, $Gd_2O_3$, the mixed oxides thereof, SiC, TiC, $Si_3N_4$ and AlN. Herein most preferred is a ceramic or glass-ceramic article, wherein at least 50 percent by weight, preferably at least 70 percent by weight of said article consist of one or more oxides selected from the group consisting of $ZrO_2$, $Al_2O_3$, $SiO_2$, MgO, $Y_2O_3$, $Cr_2O_3$, $Na_2O$, $TiO_2$, $La_2O_3$, and the mixed oxides thereof.

Preferred is a ceramic or glass-ceramic article, according to the present invention, (and especially preferred according to any ceramic or glass-ceramic article described herein as preferred) wherein said article comprises $ZrO_2$ and $Al_2O_3$. Herein further preferred is a ceramic or glass-ceramic article, wherein the mixing ratio by weight of $ZrO_2$ to $Al_2O_3$ is in the range of from 1:4 to 4:1, preferably in the range of from 3:7 to 7:3. Herein even further preferred is a ceramic or glass-ceramic article, wherein the mixing ratio by weight of $ZrO_2$ to $Al_2O_3$ is 42.6 to 57.4. Particularly preferred is a ceramic or glass-ceramic article, wherein said article consists of 42.6 percent by weight of $ZrO_2$ and 57.4 percent by weight of $Al_2O_3$.

Preferred is a ceramic or glass-ceramic article according to the present invention, (especially preferred a ceramic or glass-ceramic article described herein as preferred) comprising tetragonal stabilized, doped $ZrO_2$. Herein further preferred is a ceramic or glass-ceramic article, wherein the tetragonal stabilized doped $ZrO_2$ is $ZrO_2$ doped with at least one component selected from the group comprising $Y_2O_3$, $CeO_2$ and MgO and wherein, if selected, in particular if selected as sole component from the group, the amount of $Y_2O_3$ is preferably in the range of 1 to 7 percent by weight, the amount of $CeO_2$ is preferably in the range of 5 to 15 percent by weight and the amount of MgO is preferably in the range of 3 to 10 percent by weight based on the overall amount of $ZrO_2$. Herein most preferred is a ceramic or glass-ceramic article, wherein the amount of the component or components selected from said group is preferably sufficient to stabilize at least 50% by volume, preferably at least 75% by volume of the $ZrO_2$ in the final article in the tetragonal form.

Preferred is further a ceramic or glass-ceramic article, preferably as described herein before, (especially preferred a ceramic or glass-ceramic article described herein as preferred) wherein said article is a dental article, in particular a dental restoration or frame. Preferred is further a ceramic or glass-ceramic article, preferably as described herein before, (especially preferred a ceramic or glass-ceramic article described herein as preferred) wherein said ceramic or glass-ceramic dental article is a crown, a bridge, an inlay, an onlay or an abutment.

Preferred is further a ceramic or glass-ceramic article according to the present invention, preferably as described herein before, (and especially preferred according to any ceramic or glass-ceramic article described herein as preferred) wherein said (preferably dental) article is tooth-colored.

Preferred is further a ceramic or glass-ceramic article according to the present invention, (especially preferred a ceramic or glass-ceramic article described herein as preferred) characterized in that the article can be produced by a method according to the present invention, in particular according to a method characterized above as being preferred.

Ceramic or glass-ceramic articles according to the present invention may be used for a variety of applications. As mentioned above, they may be used in medical treatments as implants, especially in dentistry as (part of) a dental restoration or frame, especially as a crown, a bridge, an inlay, an onlay or an abutment. They may also be used in the electronic industry, for example in ceramic resistors, ceramic capacitors, in or as a substrate for integrated circuits or as insulating material. In the refractory industry they may be used as refractory material, for example for crucibles. In the chemicals industry they may be used in any application where materials with high chemical resistance, temperature resistance and low heat transmission coefficient are required. They may also be used in the aerospace industry or food industry.

BRIEF DESCRIPTION OF THE DRAWINGS

The invention will be described hereinafter in greater detail with reference to the following examples and the appended figures, in which.

DETAILED DESCRIPTION

Figure 1:
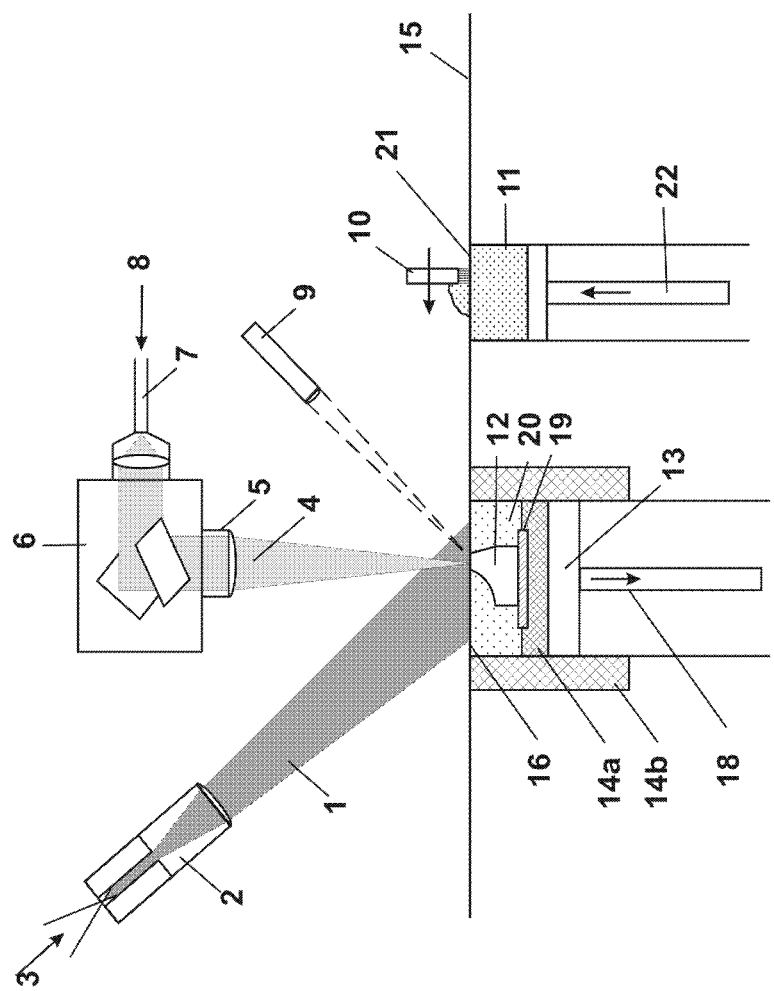
FIG. 1 is a schematic drawing of an apparatus according to the present invention for producing a ceramic or glass-ceramic article.

FIG. 1 shows an apparatus according to the present invention for producing a ceramic or glass-ceramic article. The apparatus is adapted for a method according to the present invention wherein steps (a), (b), (c), (d) and (e) are conducted. FIG. 1 shows a table top (15) with a circular opening (16). Underneath the opening (16) is a cylindrical support means (13) of the same size as opening (16) connected to a lever (18) to lower and raise support means (13). The surface of the support means (13) is lined with insulating material (14a). The ceramic or glass ceramic article (12) is mounted on a substrate (19) and the substrate is mounted on top of the insulating material (14a). The ceramic or glass ceramic article (12) is surrounded by a powder or a powder mixture (20). The powder or powder mixture (20), the ceramic or glass ceramic article (12), the substrate (19), the insulating material (14a) and the support means (13) are surrounded by a cylindrical arrangement of further insulating material (14b), such that the combined parts of insulating material (14a, 14b) form a chamber comprising the ceramic or glass ceramic article (12), the powder or powder mixture (20), the substrate (19) and the support means (13).

The table top has a further opening (21) with a powder reservoir (11). Underneath powder reservoir (11) is a further support means (13) and a further lever (22).

Above the table top is a deposition and leveling device (10) in form of a brush. The lower end of the brush consists of fibers that end close to or at the surface of the table top.

Above the table top is further shown a laser beam (3) of a $CO_2$-laser. The $CO_2$-laser itself is not shown. Laser beam (3) has a Gauss distribution. Laser beam (3) enters into a beam homogenization optic (2), which homogenizes the Gauss distribution of laser beam (3). A defocused and homogenized laser beam (1) leaves beam homogenization optic (2) and is directed onto the opening in the table top containing the ceramic or glass ceramic article (12). It is incident on the surface of the ceramic or glass ceramic article (12) and on all areas of the opening and their surrounding areas where melting in step (d) will occur during the production of the ceramic or glass ceramic article (12).

A further laser beam (8) of a Nd:YAG-laser is shown above the table top. The Nd:YAG-laser itself is not shown. Laser beam (8) is guided through an optical fiber (7) into a galvanometer scanner (6). The laser beam leaving the galvanometer scanner (6) is focused by focusing optic (5) yielding focused laser beam (4) which is incident on the surface of the ceramic or glass ceramic article (12).

A pyrometer (9) is mounted above the table top and directed onto the surface of the ceramic or glass ceramic article (12) to measure its temperate.

Laser beam (3), laser beam (8), galvanometer scanner (6), focusing optics (5) and pyrometer (9) are connected to a control device (not shown) which controls the procedure.

At the beginning of each cycle, support means (13) is lowered by means of its lever (18) by the distance identical to the desired thickness of the layer to be deposited in step (b). In step (a) a powder or a powder mixture comprising ceramic or glass-ceramic material is provided by lifting the lever (22) of powder reservoir (11).

In step (b) said powder or a powder mixture is deposited on the surface of the part of the article already produced (12) and the surrounding powder or powder mixture (20) that has not been melted in the previous cycles by means of deposition and leveling device (10). The deposition and leveling device (10) then brushes off the powder or powder mixture above the powder reservoir (11) that extends above the table top and deposits it on top of the ceramic or glass ceramic article (12) and the powder or a powder mixture (20) surrounding it. Parts of the powder or powder mixture extending above the table top are brushed off by deposition and leveling device (10). The powder of powder mixture is thereby deposited evenly.

Preheating (step (c)) is applied continuously during the whole process of producing said ceramic or glass-ceramic article (12) by laser beam (1). Laser beam (1) provides the same amount of energy per time and area on the whole surface of said layer deposited in step (b).

In step (d) laser beam (4) is guided onto said surface in a predetermined exposure pattern. Laser beam (4) is switched on when galvanometer scanner (6) directs its focus onto a region that is to be heated in step (d), and is switched off otherwise. The pyrometer (9) measures the surface temperature of the region of the surface heated by laser beam (4). The data is read out by said control device.

After the focused laser beam (4) has finished heating a certain region, the region is cooled by heat transfer from the heated region to the atmosphere, neighboring regions of said layer deposited in step (b) and the previously produced layers and to other parts of chamber formed by insulating material (14a, 14b). This cooling constitutes step (e). Laser beam (1) which serves as preheating device, continuously heats the heated regions thereby reducing the cooling rate of the heated region. Insulating material (14a, 14b) reduces the cooling rate of the whole reaction chamber and thereby also reduces the cooling rate of the heated region(s). Crystallization of the melted regions is however still fast and no waiting period has to be observed before the next cycle begins. The next cycle begins therefore as soon as step (d) of the previous cycle has ended.

Figure 2:
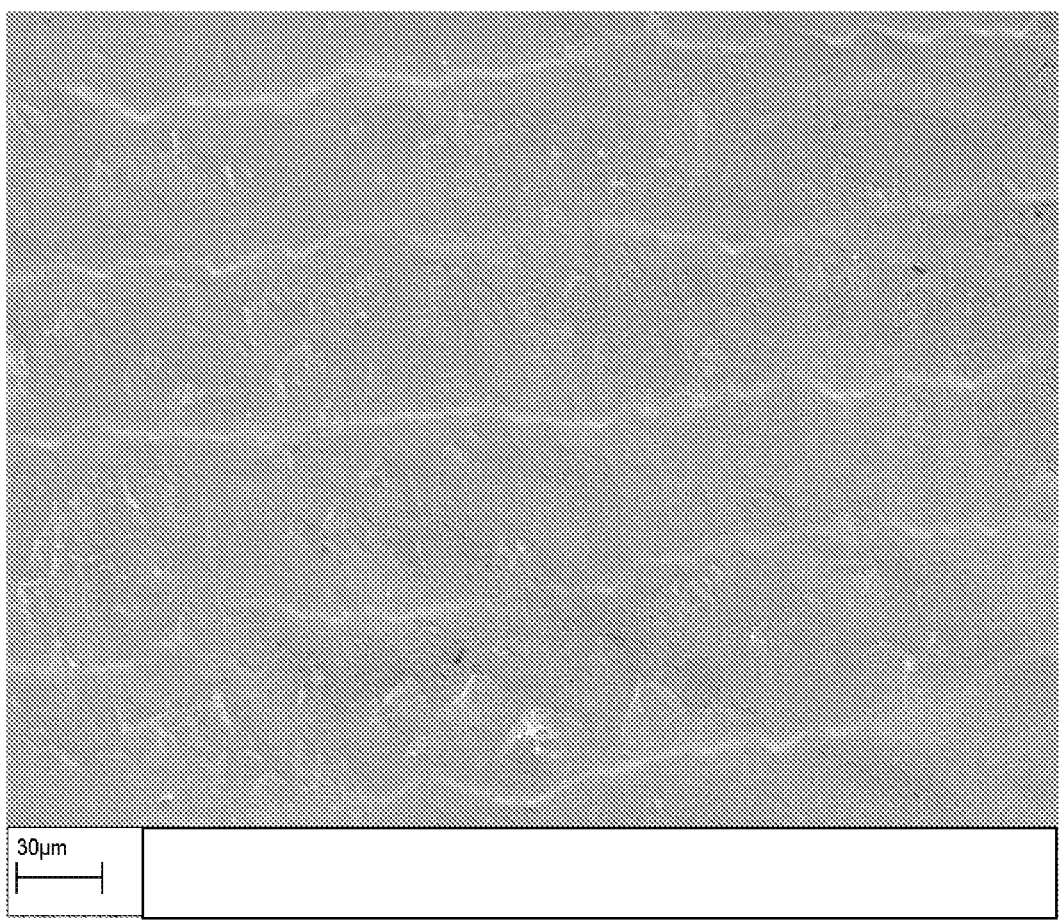
FIG. 2 is a picture taken with a light-optical microscope of the surface the last layer of the ceramic article prepared in example 1 (see below)

FIG. 2 shows the surface of the last layer of the ceramic article prepared in example 1 (see below). Apart from an irregular general roughness of the surface, the surface bears traces of the tracks melted by the laser, as indicated by the white lines running from left to the right of the picture. It is thereby evident, that the layer shown in FIG. 1 consists of -a set of adjacent, joined tracks of ceramic material.

EXAMPLES

Example 1

A powder "Zaspher 260M™" (available from Innalox bv, 5932 NB Tegelen, The Netherlands) consisting of spherical powder particles of a diameter $d_{50}$ of 35 μm prepared by condensation from the gas phase is used. The powder consists of 39.5% by weight $ZrO_2$, 1% by weight $Y_2O_3$ and 59.5% by weight $Al_2O_3$. In the selective laser melting apparatus according to FIG. 1 a layer of the powder with a thickness of approx. 100 μm is deposited on a ceramic substrate of the dimensions 18 ×18 ×3 mm³ produced by conventional sintering of the same powder. The powder layer and the substrate are preheated to a temperature of 1700° C. at a rate of 2 K/s by a $CO_2$-laser beam (1). The preheating to 1700° C. is done only once in the beginning of the build up process and then the preheating temperature is maintained approximately constant at 1700° C. during the whole build up process. The laser beam is incident on the substrate and an area surrounding the substrate and the intensity is homogeneous within the area irradiated. After a homogeneous temperature of 1700° C. is reached on the surface of the powder layer. The selected regions of the powder layer are selectively melted by means of a focused Nd:YAG-laser beam (4) with a circular focus with a diameter of 200 μm on the surface of the powder layer. To melt the powder or powder mixture in the desired regions, the focus of the laser beam (4) is moved in straight adjacent lines over the area of the substrate at a speed of 100 mm/s whereby each two adjacent lines overlap by 140 μm. The laser power is set to 60 W. The laser is switched on when it is moved over a region that is to be heated. It is switched off otherwise. After all the selected regions have been melted, the support means (13) is lowered by 50 μm, a new layer of powder is deposited and the next cycle begins. The steps powder deposition, selective melting and lowering of the platform are repeated until the whole article has been built up. The $CO_2$ laser beam (1) irradiates the ceramic article during the whole build up process, i.e. the temperature of the substrate and the emerging ceramic object is kept at approximately 1700° C. during the whole build up process. After completion of the build up process, the ceramic object and the substrate, still have a temperature of 1700° C. They are cooled to room temperature at a cooling rate of 0.2 K/s. The article prepared is separated from the substrate by sawing with a diamond wire saw. The ceramic article produced has the shape of a disc with a diameter of 14 mm and thickness of 2 mm. It is crack free and does not require any post processing. The bending strength was measured by the "ball on three points" method according to the norm DIN EN 843-1. This produced article has a bending strength of 536 MPa.

See also FIG. 2

Example 2

Powder Composition 80% $ZrO_2$, 20% $Al_2O_3$ 2.1 Preparation of Article (with Glass Infiltration, without Preheating)

A powder consisting of 80% by weight of zirconia and 20% by weight of alumina powder with a powder particle size between 25 μm and 45 μm and a $d_{50}$ value of 35 μm is prepared by mixing two powders prepared separately by crushing, grinding and sieving a solidified alumina melt and a solidified zirconia melt, respectively. In a selective laser melting apparatus a layer of the powder with a thickness of approx. 100 μm is deposited on an aluminium substrate. Subsequently a focussed $CO_2$ laser beam is used to selectively melt regions of the powder layer. The beam diameter is 300 μm on the surface of the powder layer. To melt the powder or powder mixture in the desired regions, the focus of the laser beam (4) is moved in straight adjacent lines over area of the substrate whereby each two adjacent lines overlap by 190 μm at a speed of 100 mm/s. The laser power is set to 120 W. The laser is switched on when it moves over a region that is to be heated. It is switched off otherwise. After all the selected regions have been melted, a new layer of powder of a thickness of 50 μm is deposited and the next cycle begins. These steps are repeated until the whole article has been built up. The article prepared is separated from the substrate by sawing with a diamond wire saw. The ceramic article produced contains a large number of microcracks. In order to improve the bending strength and other physical properties, a glass infiltration procedure is performed subsequently. For this purpose a glass is formed out of the following oxides:

| Component | wt % |
|---|---|
| $SiO_2$ | 21 |
| $B_2O_3$ | 24 |
| $Al_2O_3$ | 35 |
| $Li_2O$ | 15 |

| Component | wt % |
| --- | --- |
| CaO | 5 |
| Total | 100 |

For glass infiltration powder of the glass produced is placed in a crucible and the object is placed on top of the glass powder. The crucible is then heated in a furnace to a temperature of 950° C. for 1 hour. The article is subsequently cooled to ambient temperature. The article produced has the dimensions 5 mm×6 mm×45 mm. The bending strength was measured by the "ball on three points" method according to the norm DIN EN 843-1. The produced article has a bending strength of 48 MPa.

2.2 Preparation of Article (without Glass Infiltration, with Preheating)

The experimental conditions are as described in Example 2.1.

However, an additional preheating step according to step (c) of the present invention is conducted and no glass infiltration step is carried out.

The initial powder layer and the substrate are preheated to a temperature of 1700° C. at a rate of 2 K/s by a $CO_2$-laser beam. The preheating to 1700° C. is done only once in the beginning of the build up process and then the preheating temperature is maintained approximately constant at 1700° C. during the whole build up process.

The bending strength of the produced article was above 200 MPa.

Example 3

Powder Composition 80% $ZrO_2$, 20% $Al_2O_3$ 3.1 Preparation of Article (with Glass Infiltration, without Preheating), Examination of Precipitation Behaviour The experimental conditions are as described in Example 2.1 The precipitation behaviour in a region is examined in more detail, after the laser has been switched off:

It is observed that $ZrO_2$ crystals precipitate first from the melt, as soon as the temperature falls below 2200° C. This way the $ZrO_2$ content in the melt is continuously reduced during further cooling down to a temperature of 1860° C. At that temperature, the remaining melt has exactly the eutectic composition (41.5 wt. % $ZrO_2$/58.5 wt. % $Al_2O_3$). This melt represents 30.4 wt. % of the total mass of the deposited powder. When this eutectic melt finally solidifies, a fine grained two phase microstructure with grain sizes smaller than 1 μm is formed. The larger $ZrO_2$ crystals solidified earlier are embedded in this fine grained matrix.

3.2 Preparation of Article (without Glass Infiltration, with Preheating), Examination of Precipitation Behaviour The experimental conditions are as described in Example 2.2.

The observations are similar to those of Example 3.1. However, the $ZrO_2$ crystals solidifying initially are larger than those of Example 3.1.

Example 4

Powder Composition 41.5% $ZrO_2$, 58.5% $Al_2O_3$ 4.1 Preparation of Article (with Glass Infiltration, without Preheating), Examination of Precipitation Behaviour The experimental conditions are similar to those described in Example 2.1. However, an initial powder consisting of 41.5% by weight of zirconia and 58.5% by weight of alumina powder with a powder particle size between 25 μm and 45 μm and a $d_{50}$ value of 35 μm is used.

The precipitation behaviour in a region is examined in more detail, after the laser has been switched off, analogous to the examination according to example 3.1.

It is observed that essentially the complete solidified material consists at least essentially of eutectic fine grained material.

4.2 Preparation of Article (without Glass Infiltration, with Preheating), Examination of Precipitation Behaviour The experimental conditions are similar to those described in Example 2.2. However, an initial powder consisting of 41.5% by weight of zirconia and 58.5% by weight of alumina powder with a powder particle size between 25 μm and 45 μm and a $d_{50}$ value of 35 μm is used.

The precipitation behaviour in a region is examined in more detail, after the laser has been switched off, analogous to the examination according to example 3.2.

It is observed that essentially the complete solidified material consists at least essentially of eutectic fine grained material.

4.3 Comparison of Bending Strengths

The respective bending strength of the articles produced according to Examples 4.1 and 4.2, respectively, were compared.

It was observed that the bending strength of the article produced according to Example 4.2 was higher than the bending strength of the article produced according to Example 4.1.

5. Comparison Example:

The experimental conditions are similar to those described in Example 2. However, an initial powder consisting of 100% by weight of alumina powder with a powder particle size between 25 μm and 45 μm and a $d_{50}$ value of 35 μm is used.

The precipitation behaviour in a region is examined in more detail, after the laser has been switched off, analogous to the examination according to example 3.

It is observed that a rather coarse microstructure is formed (grain size >10 μm), probably because grain growth is not limited by other phases.

In the following embodiments are described which illustrate the present invention. The invention is not restricted to these embodiments. Throughout the present text, the features of preferred embodiments of the present invention (in particular preferred methods of the present invention) can be combined with features of other preferred embodiments, as long as said features do not contradict each other.

1. Method of producing a ceramic or glass-ceramic article comprising the steps of:
(a) providing a powder or a powder mixture comprising ceramic or glass-ceramic material,
(b) depositing a layer of said powder or powder mixture on a surface,
(d) heating at least one region of said layer by means of an energy beam or a plurality of energy beams to a maximum temperature such that at least a part of said ceramic or glass-ceramic material in said at least one region is melted,
(e) cooling said at least one region of said layer so that at least part of the material melted in step (d) is solidified, such that the layer is joined with said surface in said at least one region, wherein preferably during solidification in step (e) from the molten ceramic or glass-ceramic material two or more phases of distinct materials crystallize.

2. Method according to embodiment 1, wherein the method comprises the successive repetition of steps (a), (b), (d), and (e), wherein the surface of the layer produced by a preceding series of steps (a) to (e) is used in a respective subsequent step (b) as surface for the following layer.

3. Method according to any of embodiments 1 or 2, wherein the method comprises between step (b) and step (d) the following separate step:

(c) preheating of at least one region of said layer to a preheating temperature such that no part of said ceramic or glass-ceramic material in said at least one region is melted.

4. Method according to any of embodiment 2 or 3, wherein step (c) is conducted continuously and wherein if steps (a) to (e) are not repeated, step (c) is beginning before step (d) and is ending after step (d) or alternatively, if steps (a) to (e) are repeated, step (c) is beginning before step (d) is conducted for the first time and is ending after step (d) is conducted for the last time.

5. Method according to embodiment 3 or 4, wherein in step (c) the energy for preheating in step (c) is directed to the surface of said layer.

6. Method according to any of embodiments 3 to 5, wherein in step (c) the layer is preheated by means of an energy beam or a plurality of energy beams.

7. Method according to embodiment 6, wherein in step (c) said energy beam or at least one of said plurality of energy beams is directed to said layer in a predetermined exposure pattern.

8. Method according to any of embodiments 6 or 7, wherein in step (c) said energy beam or at least one of said plurality of energy beams is repeatedly directed to said at least one region of said layer in step (c).

9. Method according to any of embodiments 3 to 7, wherein one, two, a plurality or all regions of said layer are preheated in step (c) and are also heated in step (d).

10. Method according to any of embodiments 3 to 9, wherein all regions of said layer heated in step (d) are preheated in step (c).

11. Method according to any of embodiments 3 to 10, wherein said at least one region is preheated in step (c) by at least one defocused energy beam.

12. Method according to any of embodiments 3 to 11, wherein in step (c) said at least one region is preheated by laser irradiation, electron irradiation or microwave irradiation, preferably laser irradiation.

13. Method according to any of embodiments 3 to 12, wherein said preheating temperature is in the range of from 900° C. to 2000° C., preferably in the range of from 1200° C. to 1800° C.

14. Method according to any of embodiments 3 to 13, wherein said preheating temperature is in the range of from 40% to 99%, preferably in the range of from 60% to 95% of the minimum temperature in Kelvin (K) at which a crystalline part of said ceramic or glass-ceramic material in said at least one region is melted, wherein the preheating temperature preferably is in the range of from 900° C. to 2000° C., more preferably in the range of from 1200° C. to 1800° C.

15. Method according to any of embodiments 3 to 14, preferably according to embodiment 13, wherein in step (c) said at least one region is preheated by one or more laser beams, preferably laser beams of a laser selected from the group consisting of $CO_2$-laser, Nd: YAG-laser, fiber laser and diode laser.

16. Method according to any of embodiments 3 to 15, wherein in step (c) one, two, a plurality or all regions are preheated.

17. Method according to any of embodiments 6 to 16, wherein in step (c) said energy beam or said plurality of energy beams is directed to one, two, a plurality or all regions of said layer in a predetermined exposure pattern.

18. Method according to any of embodiments 3 to 15, wherein the preheating is applied continuously during the whole process of producing said ceramic or glass-ceramic article.

19. Method according to embodiment 18, wherein the whole procedure is performed in an apparatus comprising a chamber which comprises the powder or powder mixture to be used in step (b), the originally provided surface, and the ceramic or glass-ceramic article so far produced, and wherein the whole chamber and its content are preheated to the same temperature.

20. Method according to any of the preceding embodiments, wherein heating and, if appropriate preheating is conducted such that that the powder or powder mixture in some or all regions that are not heated in step (d) is not changed in chemical composition, particle size and/or flow characteristics.

21. Method according to any of the preceding embodiments, wherein said powder or powder mixture comprises components that form an eutectic system with each other, wherein preferably said powder or powder mixture comprises two, three or more ceramic components that form an eutectic system with each other, wherein preferably said powder or powder mixture comprises two, three or more ceramic components that form an eutectic system with each other, such that during solidification in step (e) from the molten ceramic or glass-ceramic material at the eutectic point of said eutectic system two or more phases of distinct materials crystallize, wherein preferably said powder or powder mixture comprises two, three or more ceramic components that form an eutectic system with each other, such that during solidification in step (e) from the molten ceramic or glass-ceramic material at the eutectic point of said eutectic system two or more phases of distinct materials crystallize, wherein the total fraction by weight of said two, three or more ceramic components that form said eutectic system with each other is at least 50%, preferably at least 70%, more preferably at least 80%, of the powder or powder mixture, wherein more preferably at least one, preferably all, of the ceramic components forming said eutectic system with another ceramic component are selected from the group consisting of $Al_2O_3$, $ZrO_2$, $Y_2O_3$, $Na_2O$, $Nb_2O_5$, $La_2O_3$, $CaO$, $SrO$, $CeO_2$, $MgO$, $SiO_2$, $TiO_2$, $Cr_2O_3$, $CuO$, $Eu_2O_3$, $Er_2O_3$, $CoO$, $Gd_2O_3$, the mixed oxides thereof, especially $MgAl_2O_4$ $Y_3Al_5O_{12}$, $Er_3Al_5O_{12}$, $NiAl_2O_4$, $LaAlO_3$ and $La_2ZrO_7$, $SiC$, $TiC$, $Si_3N_4$ and $AlN$.

22. Method according to any of the preceding embodiments, wherein at least 50 percent by weight, preferably at least 70 percent by weight of said powder or powder mixture consist of components that form an eutectic system with each other.

23. Method according to any of embodiments 21 or 22, wherein for each component of said eutectic system the fraction by weight of the component, based on the weight of the eutectic system in the powder or powder mixture, is at least 25%, preferably at least 50%, especially preferred at least 70% and most preferred at least 90% of the fraction by weight of the same component in the eutectic mixture of said eutectic system.

24. Method according to any of the preceding embodiments, wherein said powder or powder mixture comprises one or more compounds selected from the group consisting of $Al_2O_3$, $ZrO_2$, $Y_2O_3$, $Na_2O$, $Nb_2O_5$, $La_2O_3$, $CaO$, $SrO$, $CeO_2$, $MgO$, $SiO_2$, $TiO_2$, $Cr_2O_3$, $CuO$, $Eu_2O_3$, $Er_2O_3$, $CoO$, $Gd_2O_3$, the mixed oxides thereof, SiC, TiC, $Si_3N_4$ and AlN.

25. Method according to any of the preceding embodiments, preferably according to any of embodiments to 21 to 24, wherein at least 50 percent by weight, preferably at least 70 percent, more preferably at least 80% by weight, by weight of said powder or powder mixture consist of one or more compounds selected from the group consisting of $Al_2O_3$, $ZrO_2$, $Y_2O_3$, $Na_2O$, $Nb_2O_5$, $La_2O_3$, $CaO$, $SrO$, $CeO_2$, $MgO$, $SiO_2$, $TiO_2$, $Cr_2O_3$, $CuO$, $Eu_2O_3$, $Er_2O_3$, $CoO$, $Gd_2O_3$, the mixed oxides thereof (especially $MgAl_2O_4$, $Y_3Al_5O_{12}$, $Er_3Al_5O_{12}$, $NiAl_2O_4$ $LaAlO_3$ and $La_2ZrO_7$) SiC, TiC, $Si_3N_4$ and AlN.

26. Method according to any of the preceding embodiments, wherein at least 50 percent by weight, preferably at least 70 percent by weight of said powder or powder mixture consist of one or more oxides selected from the group consisting of $ZrO_2$, $Al_2O_3$, $SiO_2$, $MgO$, $Y_2O_3$, $Cr_2O_3$, $Na_2O$, $TiO_2$, $La_2O_3$, and the mixed oxides thereof, especially $MgAl_2O_4$.

27. Method according to any of the preceding embodiments, preferably according to any of embodiments 21 to 23, wherein said powder or powder mixture comprises $ZrO_2$ and $Al_2O_3$.

28. Method according to any of the preceding embodiments, preferably according to any of embodiments 21 to 23, wherein said powder or powder mixture comprises $ZrO_2$ and $Al_2O_3$, and wherein the mixing ratio by weight of $ZrO_2$ to $Al_2O_3$ is in the range of from 1:4 to 4:1, preferably in the range of from 3:7 to 7:3.

29. Method according to any of the preceding embodiments, preferably according to any of embodiments 21 to 23, wherein said powder or powder mixture comprises $ZrO_2$ and $Al_2O_3$, and wherein the mixing ratio by weight of $ZrO_2$ to $Al_2O_3$ is in the range of from 30:70 to 42.6:57.4, preferably of from 35:65 to 42.6:57.4 and especially preferred in the range of from 39:61 to 42.6:57.4

30. Method according to any of the preceding embodiments, preferably according to any of embodiments 21 to 23, wherein said powder or powder mixture comprises $ZrO_2$ and $Al_2O_3$, and wherein the mixing ratio by weight of $ZrO_2$ to $Al_2O_3$ is 42.6 to 57.4.

31. Method according to any of the preceding embodiments, wherein said powder or powder mixture consists of 42.6 percent by weight of $ZrO_2$ and 57.4 percent by weight of $Al_2O_3$.

32. Method according to any of the preceding embodiments, wherein said powder or powder mixture comprises $ZrO_2$ and $Al_2O_3$ and one or more compounds selected from the group consisting of MgO, $SiO_2$, Spinell and Mullite.

33. Method according to any of the preceding embodiments, comprising the following separate step:
Preheating of said powder or powder mixture before step (b) to a powder preheating temperature, such that no part of said ceramic or glass-ceramic material is melted.

34. Method according to embodiment 33, wherein said powder preheating temperature is in the range of from 800 to 2000° C., preferably in the range of from 900 to 1500.

35. Method according to embodiment 33, wherein said powder preheating temperature is in the range of from 30% to 90%, preferably of from 40% to 70% of the temperature in Kelvin where at least a part of said ceramic or glass-ceramic material in said at least one region is melted.

36. Method according to any of embodiments 33 to 35, wherein in step (b) said powder preheating temperature is lower than the temperature of any region of said surface in step (b).

37. Method according to any of embodiments 33 to 36, wherein said powder or powder mixture is preheated before step (b) by means of an energy radiation, preferably by means of microwave radiation or infrared radiation or a radiant heater.

38. Method according to any of the preceding embodiments, comprising the following step:
Preheating of said surface before step (b) to a surface preheating temperature such that no part of the material of said surface is melted and no part of said ceramic or glass-ceramic material in said powder or powder mixture is melted.

39. Method according to any of embodiments 1 to 35 or 37 or 38, wherein in step (b) the surface and said powder or powder mixture being deposited on the surface have the same temperature.

40. Method according to any of the preceding embodiments, wherein said energy beam or at least one energy beam of said plurality of energy beams used in step (d) is a focused energy beam, preferably a focused laser beam of a $CO_2$-laser or a Nd: YAG-laser or a focused electron beam.

41. Method according to any of the preceding embodiments, wherein in step (d) the powder or powder mixture in said region is completely melted throughout the entire thickness of said layer.

42. Method according to any of the preceding embodiments, wherein in step (d) the powder or powder mixture in said region is (completely) molten and the resulting melt is heated to a temperature that is in the range of from 1.025 to 1.5 times, preferably of from 1.05 to 1.25 times, the temperature in Kelvin of the highest melting component of said powder or powder mixture.

43. Method according to any of the preceding embodiments, wherein said powder or powder mixture comprises or consists of particles selected from the group consisting of primary particles, agglomerates, or mixtures thereof.

44. Method according to any of the preceding embodiments, wherein said powder or powder mixture comprises or consists of agglomerates obtained or obtainable by spray drying or powder jetting.

45. Method according to any of the preceding embodiments, wherein said powder or powder mixture comprises or consists of primary particles prepared by grinding, solidification from gas phase or dense sintered agglomerates obtained or obtainable by spray drying or powder jetting.

46. Method according to any of the preceding embodiments, wherein said powder or powder mixture consists of particles with a $d_{50}$ particle size in the range of from 1 to 100 µm, preferably in the range of from 15 to 70 µm 47. Method according to any of the preceding embodiments, wherein said powder or powder mixture is a bimodal or a multimodal powder mixture.

48. Method according to embodiment 47, wherein said powder or powder mixture is a bimodal powder mixture and the particles of a first fraction have a $d_{50}$ particle size in the range of from 1 to less than 15 µm, and the particles of a second fraction have a particle size in the range of from 15 to 100 µm.

49. Method according to any of the preceding embodiments, wherein after step (b), but before step (d), or if step (c) is conducted before step (c), said layer deposited in step (b) has a thickness in the range of from 5 to 200 µm, preferably in the range of from 20 to 70 µm.

50. Method according to any of the preceding embodiments, wherein during or after step (b) but before step (d) or (c), respectively, said layer is mechanically compressed.

51. Method according to any of the preceding embodiments, wherein said powder or powder mixture comprises $ZrO_2$ and at least one component selected from the group consisting of MgO, $Y_2O_3$, CaO and $CeO_2$.

52. Method according to embodiment 51, wherein said powder or powder mixture comprises $ZrO_2$ and at least one component selected from the group consisting of $Y_2O_3$, $CeO_2$ and MgO and wherein the amount of the component or components selected from said group is preferably sufficient to stabilize at least 50% by volume, preferably at least 75% by volume of the $ZrO_2$ in the final article in the tetragonal form and wherein, if selected, in particular if selected as sole component from the group, the amount of $Y_2O_3$ is preferably in the range of 1 to 7 percent by weight, the amount of $CeO_2$ is preferably in the range of 5 to 15 percent by weight and the amount of MgO is preferably in the range of 3 to 10 percent by weight based on the amount of $ZrO_2$.

53. Method according to any of embodiments 51 or 52, wherein in said ceramic or glass-ceramic article at least 50 percent by volume and preferably at least 75 percent by volume of the total volume of $ZrO_2$ in the article is tetragonal stabilized, doped $ZrO_2$.

54. Method of producing a ceramic or glass-ceramic article according to embodiment 1, comprising the steps of:

(a) providing a powder or a powder mixture comprising ceramic or glass-ceramic material, wherein said powder or powder mixture preferably comprises components that form an eutectic system with each other, (b) depositing a layer of said powder or powder mixture on a surface, (c) preheating of at least one region of said layer to a preheating temperature such that no part of said ceramic or glass-ceramic material in said at least one region is melted, (d) heating of at least one region of said layer by means of an energy beam or a plurality of energy beams to a maximum temperature such that at least a part of said ceramic or glass-ceramic material in said at least one region is melted, wherein the maximum temperature is higher than the preheating temperature, (e) cooling of said at least one region of said layer so that at least part of the material melted in step (d) is solidified, such that the layer is joined with said surface, (f) repeating of steps (a) to (e), whereby the surface of the layer produced by each foregoing series of steps (a) to (e) is used in step (b) of the repetition as surface for the following layer.

55. Method according to any of the preceding embodiments, wherein, if steps (a) to (e) are not repeated, after step (e), or if steps (a) to (e) are repeated, after the final repetition of steps (a) to (e) a glass-infiltration of the intermediate product obtained is performed at a temperature in the range of from 650° C. to 1200° C., preferably in the range of from 850° C. to 1000° C.

56. Method according to any of the preceding embodiments, wherein, if steps (a) to (e) are not repeated, after step (e), or if steps (a) to (e) are repeated, after the final repetition of steps (a) to (e) a glass-infiltration of the intermediate product obtained is performed under process conditions which are selected such that less than 5% by weight of the intermediate product is dissolved in the glass used for glass infiltration.

57. Method according to any of the preceding embodiments, wherein, if steps (a) to (e) are not repeated, after step (e), or if steps (a) to (e) are repeated, after the final repetition of steps (a) to (e), a treatment for improving bending strength is performed.

58. Method according to any of the preceding embodiments, wherein, if steps (a) to (e) are not repeated, after step (e), or if steps (a) to (e) are repeated, after the final repetition of steps (a) to (e) a glass-infiltration of the intermediate product obtained is performed and wherein the glass infiltration is performed in a vacuum.

59. Method according to any of the preceding embodiments, wherein, if steps (a) to (e) are not repeated, after step (e), or if steps (a) to (e) are repeated, after the final repetition of steps (a) to (e) a glass-infiltration of the intermediate product obtained is performed with a glass which comprises or consists of at least one compound selected from but favorably all compounds of the group consisting of $ZrO_2$, $SiO_2$, $B_2O_3$, $Al_2O_3$, $Li_2O$ and CaO.

60. Method according to any of the preceding embodiments, wherein, if steps (a) to (e) are not repeated, after step (e), or if steps (a) to (e) are repeated, after the final repetition of steps (a) to (e) a glass-infiltration of the intermediate product obtained is performed, such that said ceramic or glass-ceramic article after glass infiltration has a bending strength of at least 25 MPa, preferably of at least 250 MPa and more preferably of at least 500 MPa.

61. Method according to any of the preceding embodiments, wherein said ceramic or glass-ceramic article is produced on a substrate.

62. Method according to embodiment 61, wherein said ceramic or glass-ceramic article is produced on a substrate comprising a support means and/or a connector.

63. Method according to embodiment 62, wherein the support means or the connector has a predetermined breaking point to facilitate the separation of said ceramic or glass-ceramic article.

64. Method according to any of the preceding embodiments, wherein the process is controlled by a computer and/or a control unit.

65. Method according to embodiment 63, wherein the energy beam, in particular its intensity (power), focus, pathway, speed and/or the like is controlled and guided by a computer system.

66. Method according to any of the preceding embodiments, wherein the temperature of the surface of said layer is at least once measured by a pyrometer.

67. Method according to any of the preceding embodiments, preferably according to embodiment 65, wherein the temperature of the surface of said layer is at least once measured during step (c).

68. Method according to embodiments 66 or 67, wherein the data corresponding to the measured temperature are used for process monitoring and/or process control, preferably using a computer.

69. Method according to any of the preceding embodiments, wherein the average grain size in said produced ceramic or glass-ceramic article produced is 10 µm or smaller, preferably 2.5 µm or smaller.

70. Method according to any of the preceding embodiments, wherein said ceramic or glass-ceramic article has a bending strength of at least 25 MPa, preferably of at least 250 MPa and more preferably of at least 500 MPa.

71. Method according to any of the preceding embodiments, wherein the fracture toughness of said ceramic or glass-ceramic article is at least 4 MPa*$m^{1/2}$, preferably at least 6 MPa*$m^{1/2}$.

72. Method according to any of the preceding embodiments, wherein the material or at least part of the material solidified in step (e) has an m value maximum in the temperature range of from 1350° C. to 1500° C. of at least 0.5, preferably of at least 0.75.

73. Method according to any of the preceding embodiments, wherein the fraction of the glass phase in said ceramic or glass-ceramic article is 40 percent by volume or less, preferably 10 percent by volume or less.

74. Method according to any of the preceding embodiments, wherein the porosity of said ceramic or glass-ceramic article produced is no more than 30 percent by volume, preferably no more than 5 percent by volume.

75. Method according to any of the preceding embodiments, wherein said ceramic or glass-ceramic article is a dental article, in particular a dental restoration or frame.

76. Method according to embodiment 75, wherein said ceramic or glass-ceramic dental article is a crown, a bridge, an inlay, an onlay or an abutment.

77. Method according to any of embodiments 1 to 76, wherein said ceramic or glass-ceramic (preferably dental) article is tooth-colored.

78. Ceramic or glass-ceramic article prepared by a method according to any of the preceding embodiments.

79. Ceramic or glass-ceramic article according to embodiment 76, wherein the article is a dental article.

80. Ceramic or glass-ceramic article according to embodiment 78 to 79, wherein the article is a dental restoration or frame.

81. Ceramic or glass-ceramic article according to any of embodiments 78 to 80, wherein the article is a crown, a bridge, an inlay, an onlay or an abutment.

82. Ceramic or glass-ceramic article according to any of embodiments 78 to 81, wherein the article is tooth-colored.

83. Ceramic or glass-ceramic article according to any of embodiments 78 to 82, wherein the average particle grain size in the article is 10 μm or smaller, preferably 2.5 μm or smaller.

84. Ceramic or glass-ceramic according to any of embodiments 78 to 83, wherein said article has a bending strength of at least 25 MPa, preferably of at least 250 MPa and more preferably of at least 500 MPa.

85. Ceramic or glass-ceramic article according to any of embodiments 78 to 84, wherein the fracture toughness of the article is at least 4 MPa*m$^{1/2}$, preferably at least 6 MPa*m$^{1/2}$.

86. Ceramic or glass-ceramic article according to any of embodiments 78 to 85, comprising or consisting of material that has an m value maximum in the temperature range of from 1350° C. to 1500° C. of at least 0.5, preferably of at least 0.75.

87. Ceramic or glass-ceramic article according to any of embodiments 78 to 86, consisting of material that has a chemical solubility is 100 μg/cm$^{-2}$ or less, preferably 20 μg/cm$^{-2}$ or less.

88. Ceramic or glass-ceramic article according to any of embodiments 78 to 87, wherein the fraction of the glass phase in the article is 40 percent by volume or less, preferably 10 percent by volume or less.

89. Ceramic or glass-ceramic article according to any of embodiments 78 to 88, wherein the porosity of the article is no more than 30 percent by volume, preferably no more than 5 percent by volume.

90. Use of a ceramic or glass-ceramic article according to any of embodiments 78 to 89 as a dental article, in particular as a dental restoration or frame, or in the electronic industry.

91. Apparatus for producing a ceramic or glass-ceramic article, wherein the apparatus comprises at least one energy beam source for providing at least two energy beams operable independently of each other, at least one storage container for a powder or a powder mixture, a substrate for depositing a layer of said powder or a powder mixture, a powder deposition device for depositing a layer or layers of said powder or powder mixture on the substrate, means to direct the energy beams onto the surface or surfaces of the layer or layers of the powder or powder mixture.

92. Apparatus according to embodiment 91, wherein the apparatus comprises a pyrometer for measuring the temperature on the surface of the layer.

93. Apparatus according to any of embodiments 91 or 92, wherein the container comprises a powder or a powder mixture, which comprises components that form an eutectic system with each other.

94. Apparatus according to any of embodiments 91 or 93, comprising insulation material with a heat transfer coefficient of 20 W/(m$^2$K) or less, preferably 10 W/(m$^2$K) or less.

95. Ceramic or glass-ceramic article comprising a set of adjacent, joined layers of ceramic or glass-ceramic material, wherein said layers have a thickness in the range of from 5 to 200 μm, and/or a set of adjacent, joined tracks of ceramic or glass-ceramic material, wherein said article has a bending strength of at least 25 MPa, preferably of at least 250 MPa and more preferably of at least 500 MPa.

96. Ceramic or glass-ceramic article according to embodiment 95, wherein said layers have a thickness in the range of from 20 to 70 μm.

97. Ceramic or glass-ceramic article according to any of embodiments 95 or 96, with a bending strength of at least 25 MPa, preferably of at least 250 MPa and more preferably of at least 500 MPa.

98. Ceramic or glass-ceramic article according to any of embodiments 95 to 97, wherein the average grain size in the article is 10 μm or smaller, preferably 2.5 μm or smaller.

99. Ceramic or glass-ceramic article according to any of embodiments 95 to 98, wherein the fracture toughness of the article is at least 4 MPa*m$^{1/2}$, preferably at least 6 MPa*m$^{1/2}$.

100. Ceramic or glass-ceramic article according to any of embodiments 95 to 99, wherein the article comprises a glass phase, the fraction of the glass phase in the article being no more than 40 percent by volume, preferably no more than 10 percent by volume.

101. Ceramic or glass-ceramic article according to any of embodiments 95 to 102, wherein the article comprises a glass phase, which comprises or consists of compounds selected from the group consisting of $ZrO_2$, $SiO_2$, $B_2O_3$, $Al_2O_3$, $Li_2O$, $ZrO_2$ and $CaO$.

102. Ceramic or glass-ceramic article according to any of embodiments 95 to 101, wherein the porosity of the article is no more than 30 percent by volume, preferably no more than 5 percent by volume.

103. Ceramic or glass-ceramic article, preferably according to any of embodiments 95 to 102, comprising a set of adjacent, joined layers of ceramic or glass-ceramic material, wherein said layers have a thickness in the range of from 5 to 200 μm, and/or a set of adjacent, joined tracks of ceramic or glass-ceramic material,
wherein said ceramic or glass-ceramic material comprises components that form an eutectic system with each other.

104. Ceramic or glass-ceramic article according to any of embodiments 95 to 103, wherein at least 50 percent by weight, preferably at least 70 percent by weight, more preferably at least 80%, of said ceramic or glass-ceramic material consist of components that form an eutectic system with each other.

105. Ceramic or glass-ceramic article according to any of embodiments 103 or 104, wherein for each component of said eutectic system the fraction by weight of the component in said ceramic or glass-ceramic material, based on the weight of the eutectic system in the powder or powder mixture, is at least 25%, preferably at least 50%, especially preferred at least 70% and most preferred at least 90% of the fraction by weight of the same component in the eutectic mixture of said eutectic system.

106. Ceramic or glass-ceramic article according to any of embodiments 95 to 105, comprising one or more compounds selected from the group consisting of $Al_2O_3$, $ZrO_2$, $Y_2O_3$, $Na_2O$, $Nb_2O_5$, $La_2O_3$, $CaO$, $SrO$, $CeO_2$, $MgO$, $SiO_2$, $TiO_2$, $Cr_2O_3$, $CuO$, $Eu_2O_3$, $Er_2O_3$, $CoO$, $Gd_2O_3$, the mixed oxides thereof especially $MgAl_2O_4$, $Y_3Al_5O_{12}$, $Er_3Al_5O_{12}$, $NiAl_2O_4$, $LaAlO_3$ and $La_2ZrO_7$, SiC, TiC, $Si_3N_4$ and AlN.

107. Ceramic or glass-ceramic article according to any of embodiments 95 to 105, wherein at least 50 percent by weight, preferably at least 70 percent by weight of said article consist of one or more compounds selected from the group consisting of $Al_2O_3$, $ZrO_2$, $Y_2O_3$, $Na_2O$, $Nb_2O_5$, $La_2O_3$, $CaO$, $SrO$, $CeO_2$, $MgO$, $SiO_2$, $TiO_2$, $Cr_2O_3$, $CuO$, $Eu_2O_3$, $Er_2O_3$, $CoO$, $Gd_2O_3$, the mixed oxides thereof, especially $MgAl_2O_4$, $Y_3Al_5O_{12}$, $Er_3Al_5O_{12}$, $NiAl_2O_4$, $LaAlO_3$ and $La_2ZrO_7$, SiC, TiC, $Si_3N_4$ and AlN.

108. Ceramic or glass-ceramic article according to any of embodiments 95 to 107, wherein at least 50 percent by weight, preferably at least 70 percent by weight of said article consist of one or more oxides selected from the group consisting of $ZrO_2$, $Al_2O_3$, $SiO_2$, $MgO$, $Y_2O_3$, $Cr_2O_3$, $Na_2O$, $TiO_2$, $La_2O_3$, and the mixed oxides thereof.

109. Ceramic or glass-ceramic article according to any of embodiments 95 to 108, preferably according to any of embodiments 103 to 105, wherein said article comprises $ZrO_2$ and $Al_2O_3$.

110. Ceramic or glass-ceramic article according to any of embodiments 95 to 109, preferably according to any of embodiments 103 to 105, wherein the mixing ratio by weight of $ZrO_2$ to $Al_2O_3$ is in the range of from 1:4 to 4:1, preferably in the range of from 3:7 to 7:3.

111. Ceramic or glass-ceramic article according to any of embodiments 95 to 110, preferably according to any of embodiments 103 to 105, wherein the mixing ratio by weight of $ZrO_2$ to $Al_2O_3$ is 42.6 to 57.4.

112. Ceramic or glass-ceramic article according to any of embodiments 95 to 111, wherein said article consists of 42.6 percent by weight of $ZrO_2$ and 57.4 percent by weight of $Al_2O_3$.

113. Ceramic or glass-ceramic article according to any of embodiments 103 to 112, comprising tetragonal stabilized, doped $ZrO_2$.

114. Ceramic or glass-ceramic article according to embodiment 113, wherein the tetragonal stabilized doped $ZrO_2$ is $ZrO_2$ doped with at least one component selected from the group comprising $Y_2O_3$, $CeO_2$ and $MgO$ and wherein, if selected, in particular if selected as sole component from the group, the amount of $Y_2O_3$ is preferably in the range of 1 to 7 percent by weight, the amount of $CeO_2$ is preferably in the range of 5 to 15 percent by weight and the amount of $MgO$ is preferably in the range of 3 to 10 percent by weight based on the amount of $ZrO_2$.

115. Ceramic or glass-ceramic article according to any of embodiments 113 or 114, wherein the amount of the component or components selected from said group is preferably sufficient to stabilize at least 50% by volume, preferably at least 75% by volume of the $ZrO_2$ in the final article in the tetragonal form.

116. Ceramic or glass-ceramic article according to any of embodiments 78 to 115, wherein said article is a dental restoration or frame.

117. Ceramic or glass-ceramic article according to any of embodiments 95 to 116, wherein said article is a crown, a bridge, an inlay, an onlay or an abutment.

118. Ceramic or glass-ceramic article according to any of embodiments 95 to 117, wherein said article is tooth-colored.

119. Ceramic or glass-ceramic article, preferably according to any of embodiments 95 to 118, characterized in that the article can be produced by a method according to any of embodiments 1 to 75.

The invention claimed is:

1. Method of producing a ceramic or glass-ceramic article from a powder or powder mixture, comprising the steps of:
   (a) providing the powder or powder mixture comprising ceramic or glass-ceramic material,
   (b) depositing a layer of said powder or powder mixture on a surface,
   (d) heating at least one region of said layer by means of an energy beam or a plurality of energy beams to a maximum temperature such that at least a part of said ceramic or glass-ceramic material in said at least one region is melted,
   (e) cooling said at least one region of said layer so that at least part of the material melted in step (d) is solidified, such that the layer is joined with said surface in said at least one region,
   wherein the method includes a preheating step (c) wherein in the step (c) one or more of the at least one regions are, preheated,
   wherein the method comprises successive repetition of the steps (a), (b), (c), (d), and (e) to produce the ceramic or glass-ceramic article, wherein a successive surface of the layer produced by a preceding series of the steps (a), (b), (c), (d), and (e) is used in a respective subsequent step (b) as a surface for the following layer,
   wherein said powder or powder mixture comprises components that form an eutectic system with each other during solidification in the step (e),
   wherein, for each repetition, the step (a) starts before the step (b), the step (b) starts before the step (c), the step (c) starts before the step (d), and the step (d) starts before the step (e), and
   wherein at least 50 percent by weight of said powder or powder mixture is the eutectic system, wherein each of the components is selected from the group consisting of $Al_2O_3$, $ZrO_2$, $Y_2O_3$, $Na_2O$, $Nb_2O_5$, $La_2O_3$, $CaO$, $SrO$, $CeO_2$, $MgO$, $TiO_2$, $Cr_2O_3$, $CuO$, mixed oxides thereof, SiC, TiC, $Si_3N_4$ and AlN.

2. Method according to claim 1, wherein the step (c) further comprises preheating of the at least one region of said layer to a preheating temperature such that no part of said powder or powder mixture in said at least one region is melted.

3. Method according to claim 1, wherein the step (c) is conducted continuously, when the steps (a), (b), (c), (d), and (e) are repeated in sequence, the step (c) begins before the step (d) is conducted for the first time and ends after the step (d) is conducted for the last time.

4. Method according to claim 2, wherein in the step (c) the energy for preheating in the step (c) is directed to the surface of said layer.

5. Method according to claim 2, wherein in the step (c) said at least one region is preheated by laser irradiation, electron irradiation or microwave irradiation, preferably laser irradiation.

6. Method according to claim 2, wherein said ceramic or glass-ceramic material comprises a crystalline part, and wherein said preheating temperature of the step (c) is in the range of from 40% to 99% of the minimum temperature in Kelvin (K) at which the crystalline part of said ceramic or glass-ceramic material in said at least one region is melted, wherein the preheating temperature is in the range of from 900° C. to 2000° C.

7. Method according to claim 1, wherein for each component of said eutectic system, the fraction by weight of the each component of said eutectic system, is at least 25% by weight of said eutectic system.

8. Method according to claim 1, wherein at least 70 percent by weight of said powder or powder mixture is the eutectic system, wherein each of the components is selected from the group consisting of $Al_2O_3$, $ZrO_2$, $Y_2O_3$, $Na_2O$, $Nb_2O_5$, $La_2O_3$, CaO, SrO, $CeO_2$, MgO, $SiO_2$, $TiO_2$, $Cr_2O_3$, CuO, $Eu_2O_3$, $Er_2O_3$, CoO, $Gd_2O_3$, the mixed oxides thereof, SiC, TiC, $Si_3N_4$ and AlN.

9. Method according to claim 1, wherein said powder or powder mixture comprises $ZrO_2$ and $Al_2O_3$, and wherein the mixing ratio by weight of $ZrO_2$ to $Al_2O_3$ is in the range of from 30:70 to 42.6:57.4.

10. Method according to claim 1, wherein said powder or powder mixture comprises $ZrO_2$ and at least one component selected from the group consisting of MgO, $Y_2O_3$, CaO and $CeO_2$.

11. Method of producing a composition comprising a ceramic or glass-ceramic article according to claim 1, wherein the maximum temperature is higher than the preheating temperature.

12. Method according to claim 1, wherein an intermediate product obtained following the final repetition of steps (a), (b), (c), (d), and (e) is subjected to a glass-infiltration at a temperature in the range of from 650° C. to 1200° C.

13. The method of claim 1, wherein during solidification in the step (e) from the molten ceramic or glass-ceramic material, two or more phases of distinct materials crystallize.

14. The method of claim 1, wherein for each component of the eutectic system, the fraction by weight of each of the components is at least 25% of the fraction by weight of said eutectic system.

15. The method of claim 1, wherein each of said layers has a thickness in the range of from 5 to 200 μm.

16. The method of claim 1, wherein the components consist of $Al_2O_3$, $ZrO_2$, and at least one of the components is selected from the group consisting of $Y_2O_3$, $CeO_2$, MgO, wherein at least 50 percent by weight of said powder or powder mixture is $Al_2O_3$ and $ZrO_2$, and wherein a weight ratio of $ZrO_2$ to $Al_2O_3$ is in the range of from 3:7 to 7:3.

* * * * *

UNITED STATES PATENT AND TRADEMARK OFFICE
CERTIFICATE OF CORRECTION

PATENT NO. : 9,556,525 B2  
APPLICATION NO. : 13/389789  
DATED : January 31, 2017  
INVENTOR(S) : Stephan Dierkes et al.

Page 1 of 1

It is certified that error appears in the above-identified patent and that said Letters Patent is hereby corrected as shown below:

On the Title Page

Item [73], Assignees: delete "BEGO BREMER GOLDSCHLÄGEREI WILH, HERBST GMBH & CO. KG" and insert -- BEGO BREMER GOLDSCHLÄGEREI WILH. HERBST GMBH & CO. KG -- in place thereof.

Item [73], Assignees: delete "NEDERLANDSE ORGANISATIE VOOR TOEGEPAST NATUURWETENSCHAPPELIJK ONDERZOEK TNO INNALOX BV, Delft (NL);" and insert -- NEDERLANDSE ORGANISATIE VOOR TOEGEPAST NATUURWETENSCHAPPELIJK ONDERZOEK TNO, Da Den Haag (NL) INNALOX BV, NB Telegen (NL) -- in place thereof.

Item [73], Assignees: delete "FRAUNHOFER-GESELLSCHAFT ZUR FÖRDERUNG DER ANGEWANDTEN FORSCHUNGE E.V." and insert -- FRAUNHOFER-GESELLSCHAFT ZUR FÖRDERUNG DER ANGEWANDTEN FORSCHUNG E.V. -- in place thereof.

Signed and Sealed this  
Thirteenth Day of February, 2018

Andrei Iancu  
*Director of the United States Patent and Trademark Office*